US011590046B2

(12) United States Patent
O'Donnell et al.

(10) Patent No.: US 11,590,046 B2
(45) Date of Patent: Feb. 28, 2023

(54) FLEXIBLE MEMBERS FOR ANCHORING TO THE BODY

(71) Applicant: President and Fellows of Harvard College, Cambridge, MA (US)

(72) Inventors: Kathleen E. O'Donnell, Cambridge, MA (US); Conor J. Walsh, Cambridge, MA (US); Tiffany L. Wong, Milwaukee, WI (US)

(73) Assignee: President and Fellows of Harvard College, Cambridge, MA (US)

( * ) Notice: Subject to any disclaimer, the term of this patent is extended or adjusted under 35 U.S.C. 154(b) by 769 days.

(21) Appl. No.: 16/084,377

(22) PCT Filed: Mar. 13, 2017

(86) PCT No.: PCT/US2017/022150
§ 371 (c)(1),
(2) Date: Sep. 12, 2018

(87) PCT Pub. No.: WO2017/160751
PCT Pub. Date: Sep. 21, 2017

(65) Prior Publication Data
US 2019/0070062 A1 Mar. 7, 2019

Related U.S. Application Data

(60) Provisional application No. 62/307,545, filed on Mar. 13, 2016.

(51) Int. Cl.
*A61H 3/00* (2006.01)
*A61H 1/02* (2006.01)
(Continued)

(52) U.S. Cl.
CPC ............... *A61H 3/00* (2013.01); *A61F 5/01* (2013.01); *A61H 1/024* (2013.01); *A61H 1/0266* (2013.01);
(Continued)

(58) Field of Classification Search
CPC .......... A61H 3/00; A61H 1/00; A61H 1/0262; A63B 21/4011; A61F 5/01
See application file for complete search history.

(56) References Cited

U.S. PATENT DOCUMENTS

| 3,387,305 A | 6/1968 | Shafer |
| 3,411,511 A | 11/1968 | Marino |

(Continued)

FOREIGN PATENT DOCUMENTS

| CN | 1431084 A | 7/2003 |
| CN | 1868434 | 11/2006 |

(Continued)

OTHER PUBLICATIONS

PCT International Search Report in International Application No. PCT/US2017/022150 dated Jun. 9, 2017.
(Continued)

*Primary Examiner* — Samchuan C Yao
*Assistant Examiner* — Nathan M Le
(74) *Attorney, Agent, or Firm* — Wolf, Greenfield & Sacks, P.C.

(57) ABSTRACT

A flexible anchor member comprising a member for placement about a body part; at least one substantially inextensible textile element circumscribing the member and secured to itself or the member; and a force transfer coupler coupling a portion of the at least one substantially inextensible textile element to an actuator such that the substantially inextensible textile element constricts about the member for a duration of an applied force. Another flexible anchor mem-
(Continued)

ber comprising an outer member including a substantially inextensible textile material configured for directing a force applied by an actuator to act upon all or a portion of the body part; an inner member for positioning between the body part and the outer member, a first surface of the inner member configured for frictionally engaging the body part or intervening clothing; and at least one coupler for coupling the outer member and the inner member.

42 Claims, 20 Drawing Sheets

(51) Int. Cl.
    *A63B 21/00* (2006.01)
    *A61F 5/01* (2006.01)
    *A63B 21/04* (2006.01)
    *A61N 1/00* (2006.01)
    *A61N 1/04* (2006.01)
    *A63B 21/02* (2006.01)
    *A61F 2/68* (2006.01)

(52) U.S. Cl.
    CPC ............ *A61N 1/00* (2013.01); *A61N 1/0452* (2013.01); *A61N 1/0484* (2013.01); *A63B 21/4011* (2015.10); *A61F 2/68* (2013.01); *A61H 1/0262* (2013.01); *A61H 1/0274* (2013.01); *A61H 2003/007* (2013.01); *A61H 2201/165* (2013.01); *A61H 2201/1647* (2013.01); *A61H 2201/1697* (2013.01); *A61H 2201/5061* (2013.01); *A61H 2201/5064* (2013.01); *A61H 2201/5071* (2013.01); *A61H 2201/5084* (2013.01); *A61H 2201/5092* (2013.01); *A61H 2201/5097* (2013.01); *A61H 2230/25* (2013.01); *A61H 2230/255* (2013.01); *A61H 2230/50* (2013.01); *A61H 2230/65* (2013.01); *A61H 2230/655* (2013.01); *A63B 21/023* (2013.01); *A63B 21/0421* (2013.01); *A63B 21/4007* (2015.10); *A63B 21/4009* (2015.10); *A63B 21/4017* (2015.10); *A63B 21/4019* (2015.10); *A63B 2213/004* (2013.01); *A63B 2220/13* (2013.01); *A63B 2220/40* (2013.01); *A63B 2220/51* (2013.01); *A63B 2220/805* (2013.01); *A63B 2225/50* (2013.01); *A63B 2230/50* (2013.01); *A63B 2230/65* (2013.01)

(56) References Cited

U.S. PATENT DOCUMENTS

| | | |
|---|---|---|
| 3,831,467 A | 8/1974 | Moore |
| 4,023,215 A | 5/1977 | Moore |
| 4,252,112 A | 2/1981 | Joyce |
| 4,370,977 A | 2/1983 | Mauldin et al. |
| 4,682,776 A | 7/1987 | Mitchell et al. |
| 4,697,808 A | 10/1987 | Larson et al. |
| 4,724,827 A | 2/1988 | Schenck |
| 4,760,850 A | 8/1988 | Phillips et al. |
| 5,020,790 A | 6/1991 | Beard et al. |
| 5,282,460 A | 2/1994 | Boldt |
| 5,485,402 A | 1/1996 | Smith et al. |
| 5,584,799 A | 12/1996 | Gray |
| 5,599,283 A | 2/1997 | Lindenmeyer et al. |
| 5,667,461 A | 9/1997 | Hall |
| 5,807,298 A * | 9/1998 | Palumbo ............ A61F 13/062 602/26 |
| 5,826,578 A | 10/1998 | Curchod |
| 5,865,714 A | 2/1999 | Marlowe |
| 5,865,770 A | 2/1999 | Schectman |
| 5,955,667 A | 9/1999 | Fyfe |
| 6,123,649 A | 9/2000 | Lee et al. |
| 6,129,691 A | 10/2000 | Ruppert |
| 6,168,634 B1 | 1/2001 | Sclunitz |
| 6,213,922 B1 | 4/2001 | Afanasenko et al. |
| 6,500,138 B1 | 12/2002 | Irby et al. |
| 6,517,503 B1 | 2/2003 | Naft et al. |
| 6,633,783 B1 | 10/2003 | Dariush et al. |
| 6,635,024 B2 | 10/2003 | Hatton et al. |
| 6,666,831 B1 | 12/2003 | Edgerton et al. |
| 6,689,075 B2 | 2/2004 | West |
| 6,741,911 B2 | 5/2004 | Simmons |
| 6,783,555 B2 | 8/2004 | Kuhn et al. |
| 6,790,165 B2 | 9/2004 | Huang |
| 6,796,926 B2 | 9/2004 | Reinkensmeyer et al. |
| 6,812,624 B1 | 11/2004 | Pei et al. |
| 6,955,692 B2 | 10/2005 | Grundei |
| 6,989,669 B2 | 1/2006 | Low et al. |
| 7,034,432 B1 | 4/2006 | Pelrine et al. |
| 7,034,527 B2 | 4/2006 | Low et al. |
| 7,049,732 B2 | 5/2006 | Pei et al. |
| 7,056,297 B2 | 6/2006 | Dohnu et al. |
| 7,064,472 B2 | 6/2006 | Pelrine et al. |
| 7,090,650 B2 | 8/2006 | Ou et al. |
| 7,153,242 B2 | 12/2006 | Goffer |
| 7,153,246 B2 | 12/2006 | Koscielny et al. |
| 7,166,953 B2 | 1/2007 | Heim et al. |
| 7,190,141 B1 | 3/2007 | Ashrafiuon et al. |
| 7,199,501 B2 | 4/2007 | Pei et al. |
| 7,211,937 B2 | 5/2007 | Kornbluh et al. |
| 7,224,106 B2 | 5/2007 | Pei et al. |
| 7,229,390 B2 | 6/2007 | Fujii et al. |
| 7,233,097 B2 | 6/2007 | Rosenthal et al. |
| 7,252,644 B2 | 8/2007 | Dewald et al. |
| 7,259,503 B2 | 8/2007 | Pei et al. |
| 7,259,553 B2 | 8/2007 | Arns, Jr. et al. |
| 7,307,418 B2 | 12/2007 | Low et al. |
| 7,331,906 B2 | 2/2008 | He et al. |
| 7,341,295 B1 | 3/2008 | Veatch et al. |
| 7,355,519 B2 | 4/2008 | Grold et al. |
| 7,367,958 B2 | 5/2008 | McBean et al. |
| 7,368,862 B2 | 5/2008 | Pelrine et al. |
| 7,378,878 B2 | 5/2008 | Pelrine et al. |
| 7,390,309 B2 | 6/2008 | Dariush |
| 7,410,471 B1 | 8/2008 | Campbell et al. |
| 7,411,332 B2 | 8/2008 | Kornbluh et al. |
| 7,429,253 B2 | 9/2008 | Shimada et al. |
| 7,436,099 B2 | 10/2008 | Pei et al. |
| 7,445,606 B2 | 11/2008 | Rastegar et al. |
| 7,456,549 B2 | 11/2008 | Heim et al. |
| 7,476,185 B2 | 1/2009 | Drennan |
| 7,494,450 B2 | 2/2009 | Solomon |
| 7,521,840 B2 | 4/2009 | Heim |
| 7,521,847 B2 | 4/2009 | Heim |
| 7,537,573 B2 | 5/2009 | Horst |
| 7,549,969 B2 | 6/2009 | van den Bogert |
| 7,567,681 B2 | 7/2009 | Pelrine et al. |
| 7,578,799 B2 | 8/2009 | Thorsteinsson et al. |
| 7,595,580 B2 | 9/2009 | Heim |
| 7,598,651 B2 | 10/2009 | Kornbluh et al. |
| 7,598,652 B2 | 10/2009 | Kornbluh et al. |
| 7,626,319 B2 | 12/2009 | Heim |
| 7,650,204 B2 | 1/2010 | Dariush |
| 7,652,386 B2 | 1/2010 | Donelan et al. |
| 7,654,973 B2 | 2/2010 | Firsov |
| 7,679,267 B2 | 3/2010 | Heim |
| 7,684,896 B2 | 3/2010 | Dariush |
| 7,705,521 B2 | 4/2010 | Pelrine et al. |
| 7,737,685 B2 | 6/2010 | Low et al. |
| 7,750,532 B2 | 7/2010 | Heim |
| 7,758,481 B2 | 7/2010 | Drennan |
| 7,774,177 B2 | 8/2010 | Dariush |
| 7,775,999 B2 | 8/2010 | Brown |
| 7,785,279 B2 | 8/2010 | Sankai |
| 7,785,656 B2 | 8/2010 | Pei et al. |
| 7,787,646 B2 | 8/2010 | Pelrine et al. |
| 7,804,227 B2 | 9/2010 | Pelrine et al. |
| 7,857,774 B2 | 12/2010 | Sankai |
| 7,860,562 B2 | 12/2010 | Endo et al. |

(56) References Cited

U.S. PATENT DOCUMENTS

| | | |
|---|---|---|
| 7,883,546 B2 | 2/2011 | Kazerooni et al. |
| 7,887,471 B2 | 2/2011 | McSorley |
| 7,897,168 B2 | 3/2011 | Chen et al. |
| 7,911,761 B2 | 3/2011 | Biggs et al. |
| 7,915,790 B2 | 3/2011 | Heim et al. |
| 7,918,808 B2 | 4/2011 | Simmons |
| 7,921,541 B2 | 4/2011 | Pei et al. |
| 7,923,064 B2 | 4/2011 | Pelrien et al. |
| 7,923,902 B2 | 4/2011 | Heim |
| 7,947,004 B2 | 5/2011 | Kazerooni et al. |
| 7,952,261 B2 | 5/2011 | Lipton et al. |
| 7,985,193 B2 | 6/2011 | Thorsteinsson et al. |
| 7,977,923 B2 | 7/2011 | Pelrine et al. |
| 7,981,508 B1 | 7/2011 | Sharma et al. |
| 7,990,022 B2 | 8/2011 | Heim |
| 7,998,040 B2 | 8/2011 | Kram et al. |
| 8,048,007 B2 | 11/2011 | Roy |
| 8,057,410 B2 | 11/2011 | Angold et al. |
| 8,058,861 B2 | 11/2011 | Pelrine et al. |
| 8,060,337 B2 | 11/2011 | Kulach et al. |
| 8,075,633 B2 | 12/2011 | Herr et al. |
| 8,083,644 B2 | 12/2011 | Purdy et al. |
| 8,096,965 B2 | 1/2012 | Goffer et al. |
| 8,114,034 B2 | 2/2012 | Ikeuchi et al. |
| 8,125,755 B2 | 2/2012 | Garcia et al. |
| 8,127,437 B2 | 3/2012 | Lipton et al. |
| 8,142,370 B2 | 3/2012 | Weinberg et al. |
| 8,147,436 B2 | 4/2012 | Agrawal et al. |
| 8,164,232 B2 | 4/2012 | Kornbluh et al. |
| 8,183,739 B2 | 5/2012 | Heim |
| 8,222,799 B2 | 7/2012 | Polyakov et al. |
| 8,231,687 B2 | 7/2012 | Bedard et al. |
| 8,235,869 B2 | 8/2012 | Rastegar et al. |
| 8,246,559 B2 | 8/2012 | Hoffmnan et al. |
| 8,248,750 B2 | 8/2012 | Biggs et al. |
| 8,274,244 B2 | 9/2012 | Bhugra et al. |
| 8,283,839 B2 | 10/2012 | Heim |
| 8,287,477 B1 | 10/2012 | Herr et al. |
| 8,292,836 B2 | 10/2012 | Matsuoka et al. |
| 8,299,634 B2 | 10/2012 | Donelan et al. |
| 8,311,623 B2 | 11/2012 | Sanger |
| 8,316,526 B2 | 11/2012 | Pei et al. |
| 8,316,719 B2 | 11/2012 | Majidi et al. |
| 8,323,355 B2 | 12/2012 | Latour |
| 8,325,458 B2 | 12/2012 | Prahlad et al. |
| 8,348,875 B2 | 1/2013 | Goffer et al. |
| 8,376,971 B1 | 2/2013 | Herr et al. |
| 8,409,117 B2 | 4/2013 | Cheng et al. |
| 8,436,508 B2 | 5/2013 | Kornbluh et al. |
| 8,438,757 B2 | 5/2013 | Roser |
| 8,460,001 B1 | 6/2013 | Chuang |
| 8,467,904 B2 | 6/2013 | Dariush |
| 8,488,295 B2 | 7/2013 | Garcia et al. |
| 8,508,109 B2 | 8/2013 | Pelrine et al. |
| 8,551,029 B1 | 10/2013 | Herr et al. |
| 8,551,184 B1 | 10/2013 | Herr |
| 8,562,691 B2 | 10/2013 | Endo et al. |
| 8,564,926 B2 | 10/2013 | Prahlad et al. |
| 8,573,982 B1 | 11/2013 | Chuang |
| 8,585,620 B2 | 11/2013 | McBean et al. |
| 8,597,369 B2 | 12/2013 | Hansen et al. |
| 8,608,479 B2 | 12/2013 | Liu |
| 8,608,674 B2 | 12/2013 | Krebs et al. |
| 8,622,938 B2 | 1/2014 | Sankai |
| 8,663,133 B2 | 3/2014 | Johnson et al. |
| 8,665,578 B2 | 3/2014 | Pelrine et al. |
| 8,679,575 B2 | 3/2014 | Biggs et al. |
| 8,715,208 B2 | 5/2014 | Hodgins et al. |
| 8,766,925 B2 | 6/2014 | Perlin et al. |
| 8,764,850 B2 | 7/2014 | Hansen et al. |
| 8,773,148 B2 | 7/2014 | Sankai et al. |
| 8,847,611 B2 | 9/2014 | Ulmen et al. |
| 8,905,955 B2 | 12/2014 | Goffer et al. |
| 8,920,517 B2 | 12/2014 | Smith et al. |
| 8,926,534 B2 | 1/2015 | McBean et al. |
| 8,938,289 B2 | 1/2015 | Einav et al. |
| 8,961,439 B2 | 2/2015 | Yang et al. |
| 8,975,888 B2 | 3/2015 | Pelrine et al. |
| 8,981,621 B2 | 3/2015 | Pelrine et al. |
| 8,986,233 B2 | 3/2015 | Aoki et al. |
| 9,044,346 B2 | 6/2015 | Langlois et al. |
| 9,072,941 B2 | 7/2015 | Duda et al. |
| 9,101,323 B2 | 8/2015 | Einarsson et al. |
| 9,144,528 B2 | 9/2015 | Agrawal et al. |
| 9,149,370 B2 | 10/2015 | Herr et al. |
| 9,195,794 B2 | 11/2015 | Dariush |
| 9,198,821 B2 | 12/2015 | Unluhisarcikli et al. |
| 9,221,177 B2 | 12/2015 | Herr et al. |
| 9,227,108 B1 | 1/2016 | Chuang |
| 9,228,822 B2 | 1/2016 | Majidi et al. |
| 9,231,186 B2 | 1/2016 | Busgen et al. |
| 9,266,233 B2 | 2/2016 | Kornbluh et al. |
| 9,333,097 B2 | 5/2016 | Herr et al. |
| 9,351,900 B2 | 5/2016 | Walsh et al. |
| 9,387,096 B2 | 6/2016 | Sverrisson et al. |
| 9,403,272 B2 | 8/2016 | Kornbluh et al. |
| 9,427,864 B2 | 8/2016 | Kornbluh et al. |
| 10,028,881 B2 | 7/2018 | Yamamoto et al. |
| 10,115,319 B2 | 10/2018 | Walsh et al. |
| 10,278,883 B2 | 5/2019 | Walsh et al. |
| 10,427,293 B2 | 10/2019 | Asbeck et al. |
| 10,434,030 B2 | 10/2019 | Asbeck et al. |
| 2001/0007845 A1 | 7/2001 | Afanasenko et al. |
| 2003/0009120 A1 | 1/2003 | MacAllister |
| 2003/0030397 A1 | 2/2003 | Simmons |
| 2003/0064869 A1 | 4/2003 | Reinkensmeyer et al. |
| 2003/0092545 A1 | 5/2003 | Koscielny et al. |
| 2003/0096310 A1 | 5/2003 | Hansen et al. |
| 2003/0120183 A1 | 6/2003 | Simmons |
| 2003/0125781 A1 | 7/2003 | Dohno et al. |
| 2004/0043879 A1 | 3/2004 | Huang |
| 2004/0064195 A1 | 4/2004 | Herr |
| 2004/0087418 A1 | 5/2004 | Eldridge |
| 2004/0106881 A1 | 6/2004 | McBean et al. |
| 2004/0116260 A1 | 7/2004 | Drennan |
| 2004/0147378 A1 | 7/2004 | Conklin et al. |
| 2004/0191321 A1 | 9/2004 | Guan et al. |
| 2004/0204294 A2 | 10/2004 | Wilkinson et al. |
| 2005/0010150 A1 | 1/2005 | Firsov |
| 2005/0049865 A1 | 3/2005 | Yaxin et al. |
| 2005/0070834 A1 | 3/2005 | Herr et al. |
| 2005/0101448 A1 | 5/2005 | He et al. |
| 2005/0107725 A1 | 5/2005 | Wild |
| 2005/0157893 A1 | 7/2005 | Pelrine et al. |
| 2005/0184878 A1 | 8/2005 | Grold et al. |
| 2005/0288157 A1 | 12/2005 | Santos-Munne et al. |
| 2006/0079817 A1 | 4/2006 | Dewald et al. |
| 2006/0084899 A1* | 4/2006 | Verkade ............... A61F 5/0111 602/27 |
| 2006/0108755 A1 | 5/2006 | Smyler et al. |
| 2006/0136206 A1 | 6/2006 | Ariu et al. |
| 2006/0167396 A1* | 7/2006 | Berger ............... A63B 71/1225 602/5 |
| 2006/0192465 A1 | 8/2006 | Kornbluh et al. |
| 2006/0249315 A1 | 11/2006 | Herr et al. |
| 2007/0004570 A1 | 1/2007 | Afanasenko et al. |
| 2007/0004571 A1 | 1/2007 | Gonzalez |
| 2007/0066918 A1 | 3/2007 | Dewald et al. |
| 2007/0111868 A1 | 5/2007 | Fujii et al. |
| 2007/0123997 A1 | 5/2007 | Herr et al. |
| 2007/0135279 A1 | 6/2007 | Purdy et al. |
| 2007/0276270 A1 | 11/2007 | Tran |
| 2008/0000317 A1 | 1/2008 | Patton et al. |
| 2008/0039756 A1 | 2/2008 | Thorsteinsson et al. |
| 2008/0062589 A1 | 3/2008 | Drabing |
| 2008/0066272 A1* | 3/2008 | Hammerslag ......... A43C 11/14 24/712 |
| 2008/0071386 A1 | 3/2008 | McBean et al. |
| 2008/0075930 A1 | 3/2008 | Kornbluh et al. |
| 2008/0097269 A1 | 4/2008 | Weinberg et al. |
| 2008/0156363 A1 | 7/2008 | Ikeuchi et al. |
| 2008/0173365 A1 | 7/2008 | Unger et al. |
| 2008/0218132 A1 | 9/2008 | Pelrine et al. |
| 2008/0224564 A1 | 9/2008 | Pelrine et al. |

(56) References Cited

U.S. PATENT DOCUMENTS

| | | |
|---|---|---|
| 2008/0255488 A1 | 10/2008 | Agrawal et al. |
| 2008/0289952 A1 | 11/2008 | Pelrine et al. |
| 2008/0294019 A1 | 11/2008 | Tran |
| 2008/0300118 A1 | 12/2008 | Wehrell |
| 2009/0042702 A1 | 2/2009 | Toronto et al. |
| 2009/0221928 A1 | 9/2009 | Einav et al. |
| 2009/0255531 A1 | 10/2009 | Johnson et al. |
| 2009/0256817 A1 | 10/2009 | Perlin et al. |
| 2009/0306548 A1 | 12/2009 | Bhugra et al. |
| 2009/0319054 A1 | 12/2009 | Sankai |
| 2010/0000547 A1 | 1/2010 | Johnson et al. |
| 2010/0007240 A1 | 1/2010 | Kornbluh et al. |
| 2010/0024180 A1 | 2/2010 | Pei et al. |
| 2010/0026143 A1 | 2/2010 | Pelrine et al. |
| 2010/0030343 A1 | 2/2010 | Hansen et al. |
| 2010/0038983 A1 | 2/2010 | Bhugra et al. |
| 2010/0056966 A1 | 3/2010 | Toth |
| 2010/0144490 A1 | 6/2010 | Purdy et al. |
| 2010/0152630 A1 | 6/2010 | Matsuoka et al. |
| 2010/0185259 A1 | 7/2010 | Shiba et al. |
| 2010/0185301 A1 | 7/2010 | Hansen et al. |
| 2010/0204804 A1 | 8/2010 | Garrec |
| 2010/0271051 A1 | 10/2010 | Sankai et al. |
| 2010/0274364 A1 | 10/2010 | Pacanowsky et al. |
| 2010/0280628 A1 | 11/2010 | Sankai |
| 2010/0286796 A1 | 11/2010 | Clausen |
| 2010/0298834 A1 | 11/2010 | Hildebrandt |
| 2010/0319215 A1 | 12/2010 | Roser |
| 2010/0324698 A1 | 12/2010 | Sverrisson et al. |
| 2011/0004322 A1 | 1/2011 | Sankai |
| 2011/0009793 A1 | 1/2011 | Lucero et al. |
| 2011/0022349 A1 | 1/2011 | Kulach et al. |
| 2011/0033835 A1 | 1/2011 | Endo et al. |
| 2011/0025170 A1 | 2/2011 | Rosenthal et al. |
| 2011/0040216 A1 | 2/2011 | Herr et al. |
| 2011/0062948 A1 | 3/2011 | Arns, Jr. et al. |
| 2011/0071647 A1 | 3/2011 | Mahon |
| 2011/0093089 A1 | 4/2011 | Martin |
| 2011/0105966 A1 | 5/2011 | Kazerooni et al. |
| 2011/0150966 A1 | 5/2011 | Kazerooni et al. |
| 2011/0152696 A1 | 6/2011 | Ryan |
| 2011/0154641 A1 | 6/2011 | Pelrine et al. |
| 2011/0155307 A1 | 6/2011 | Pelrine et al. |
| 2011/0174524 A1 | 7/2011 | Sharma et al. |
| 2011/0193362 A1 | 8/2011 | Prahlad et al. |
| 2011/0201978 A1 | 8/2011 | Jeon et al. |
| 2011/0209337 A1 | 9/2011 | Pei et al. |
| 2011/0245738 A1 | 10/2011 | Agrawal et al. |
| 2011/0282255 A1 | 11/2011 | Nace |
| 2011/0295384 A1 | 12/2011 | Herr et al. |
| 2011/0295385 A1 | 12/2011 | Herr et al. |
| 2011/0313331 A1 | 12/2011 | Dehez et al. |
| 2012/0019223 A1 | 1/2012 | Pelrine et al. |
| 2012/0023638 A1 | 2/2012 | Leicester |
| 2012/0056903 A1 | 3/2012 | Shinohara et al. |
| 2012/0071797 A1 | 3/2012 | Aoki et al. |
| 2012/0100286 A1 | 4/2012 | Sharma et al. |
| 2012/0109031 A1 | 5/2012 | Vollbrecht et al. |
| 2012/0120544 A1 | 5/2012 | Pelrine et al. |
| 2012/0128960 A1 | 5/2012 | Busgen et al. |
| 2012/0157902 A1* | 6/2012 | Castillo ............... A61F 5/0123 602/26 |
| 2012/0165709 A1 | 6/2012 | Goffer et al. |
| 2012/0169184 A1 | 7/2012 | Pelrine et al. |
| 2012/0177934 A1 | 7/2012 | Vogel et al. |
| 2012/0179075 A1 | 7/2012 | Perry et al. |
| 2012/0181896 A1 | 7/2012 | Kronbluh et al. |
| 2012/0185052 A1 | 7/2012 | Lefeber |
| 2012/0209152 A1 | 8/2012 | Cordo |
| 2012/0238914 A1 | 9/2012 | Goldfield et al. |
| 2012/0248942 A1 | 10/2012 | Biggs et al. |
| 2012/0253234 A1 | 10/2012 | Yang et al. |
| 2012/0271207 A1 | 10/2012 | Schoen et al. |
| 2012/0279175 A1 | 11/2012 | Biggs et al. |
| 2012/0289870 A1 | 11/2012 | Hsiao-Wecksler et al. |
| 2012/0330198 A1 | 12/2012 | Patoglu |
| 2013/0013085 A1 | 1/2013 | Smith et al. |
| 2013/0019749 A1 | 1/2013 | Hufton et al. |
| 2013/0040783 A1 | 2/2013 | Duda et al. |
| 2013/0041617 A1 | 2/2013 | Pease et al. |
| 2013/0045530 A1 | 2/2013 | Gracias et al. |
| 2013/0058001 A1 | 3/2013 | Prahlad et al. |
| 2013/0079686 A1 | 3/2013 | Sessions |
| 2013/0093439 A1 | 4/2013 | Ulmen et al. |
| 2013/0102935 A1 | 4/2013 | Kazerooni et al. |
| 2013/0123672 A1 | 5/2013 | Goffer et al. |
| 2013/0130866 A1 | 5/2013 | Wehrell |
| 2013/0131555 A1 | 5/2013 | Hook |
| 2013/0158444 A1 | 6/2013 | Herr et al. |
| 2013/0165817 A1 | 6/2013 | Horst et al. |
| 2013/0179154 A1 | 7/2013 | Okuno |
| 2013/0186699 A1 | 7/2013 | Prahald et al. |
| 2013/0211295 A1 | 8/2013 | Johnson et al. |
| 2013/0225371 A1 | 8/2013 | Harrer et al. |
| 2013/0226048 A1 | 8/2013 | Unluhisarcikli et al. |
| 2013/0230667 A1 | 9/2013 | Sharma et al. |
| 2013/0237884 A1 | 9/2013 | Kazerooni et al. |
| 2013/0245512 A1 | 9/2013 | Goffer et al. |
| 2013/0253385 A1 | 9/2013 | Goffer et al. |
| 2013/0261513 A1 | 10/2013 | Goffer et al. |
| 2013/0261766 A1 | 10/2013 | Langlois et al. |
| 2013/0268256 A1 | 10/2013 | Dariush |
| 2013/0274640 A1 | 10/2013 | Butters et al. |
| 2013/0288863 A1 | 10/2013 | Yamamoto et al. |
| 2013/0289452 A1 | 10/2013 | Smith et al. |
| 2013/0296746 A1 | 11/2013 | Herr et al. |
| 2013/0307370 A1 | 11/2013 | Jenninger et al. |
| 2013/0310979 A1 | 11/2013 | Herr et al. |
| 2013/0312541 A1 | 11/2013 | Majidi et al. |
| 2013/0328440 A1 | 12/2013 | Kornbluh et al. |
| 2014/0046455 A1 | 2/2014 | Herr et al. |
| 2014/0194781 A1 | 7/2014 | Einarsson et al. |
| 2014/0213951 A1 | 7/2014 | Pietrusisnki et al. |
| 2014/0277739 A1 | 9/2014 | Kornbluh et al. |
| 2014/0358040 A1 | 12/2014 | Kim et al. |
| 2015/0099945 A1 | 4/2015 | Hawkins, III et al. |
| 2015/0142130 A1 | 5/2015 | Goldfarb et al. |
| 2015/0173993 A1 | 6/2015 | Walsh et al. |
| 2015/0266180 A1 | 9/2015 | Kornbluh et al. |
| 2015/0266181 A1 | 9/2015 | Kornbluh et al. |
| 2015/0297934 A1 | 10/2015 | Agrawal et al. |
| 2015/0298765 A1 | 10/2015 | Golden, Jr. |
| 2015/0321339 A1 | 11/2015 | Asbeck et al. |
| 2015/0321399 A1 | 11/2015 | Hong et al. |
| 2016/0101516 A1 | 4/2016 | Kornbluh et al. |
| 2016/0101517 A1 | 4/2016 | Kornbluh et al. |
| 2016/0107309 A1 | 4/2016 | Walsh et al. |
| 2016/0220438 A1 | 8/2016 | Walsh et al. |
| 2016/0278948 A1 | 9/2016 | Piercy et al. |
| 2016/0284231 A1 | 9/2016 | Walsh et al. |
| 2016/0346156 A1 | 12/2016 | Walsh et al. |
| 2017/0027735 A1 | 2/2017 | Walsh et al. |
| 2017/0163435 A1 | 6/2017 | Ehsani et al. |
| 2017/0176167 A1 | 6/2017 | Keller et al. |
| 2017/0202724 A1 | 7/2017 | Walsh et al. |
| 2018/0008502 A1 | 1/2018 | Asbeck et al. |
| 2018/0056104 A1 | 3/2018 | Cromie et al. |
| 2018/0370020 A1 | 12/2018 | Murakami et al. |
| 2019/0008714 A1 | 1/2019 | Murakami et al. |
| 2019/0021933 A1 | 1/2019 | Murakami et al. |
| 2019/0029912 A1 | 1/2019 | Murakami et al. |
| 2019/0060156 A1 | 2/2019 | Swift et al. |
| 2019/0060157 A1 | 2/2019 | Lamb et al. |

FOREIGN PATENT DOCUMENTS

| | | |
|---|---|---|
| CN | 101404968 A | 4/2009 |
| CN | 102596133 A | 7/2012 |
| CN | 202342034 | 7/2012 |
| CN | 101175456 | 3/2013 |
| CN | 102327173 | 5/2013 |
| CN | 104869969 A | 8/2015 |
| CN | 105266939 A | 1/2016 |
| DE | 19944139 | 4/2001 |

(56) References Cited

FOREIGN PATENT DOCUMENTS

| | | |
|---|---|---|
| EP | 0016268 | 10/1980 |
| EP | 0141640 | 10/1984 |
| EP | 0302148 | 2/1989 |
| EP | 0509723 | 10/1992 |
| EP | 1306792 | 5/2003 |
| EP | 1324403 | 7/2003 |
| EP | 1260201 | 12/2008 |
| EP | 2226053 | 9/2010 |
| EP | 1842518 | 9/2011 |
| EP | 1589059 | 6/2012 |
| EP | 2497610 | 9/2012 |
| EP | 2548543 | 1/2013 |
| EP | 1550689 | 4/2013 |
| EP | 2649976 | 10/2013 |
| JP | H07163607 | 6/1995 |
| JP | 2002301124 | 10/2002 |
| JP | 2005000500 | 1/2005 |
| JP | 2007000391 | 1/2007 |
| JP | 2008/067762 | 3/2008 |
| JP | 4345025 | 10/2009 |
| JP | 2010042069 | 2/2010 |
| JP | 2010/051416 | 3/2010 |
| JP | 4424269 | 3/2010 |
| JP | 2010075656 | 4/2010 |
| JP | 4582523 | 11/2010 |
| JP | 2011/036375 | 2/2011 |
| JP | 4848260 | 12/2011 |
| JP | 2012/192013 | 10/2012 |
| JP | 2013146328 | 8/2013 |
| JP | 2013-208397 A | 10/2013 |
| JP | 2014018536 | 2/2014 |
| JP | 2014034145 | 3/2014 |
| KR | 2016-0025899 A | 3/2016 |
| WO | WO 00/12041 A2 | 3/2000 |
| WO | WO2004/017890 | 3/2004 |
| WO | WO2004/039292 | 5/2004 |
| WO | WO2004/047928 | 6/2004 |
| WO | WO2005/102208 | 11/2005 |
| WO | WO2011/008934 | 1/2011 |
| WO | WO2011/026086 | 3/2011 |
| WO | WO2011/030641 | 3/2011 |
| WO | WO 2011/126985 | 10/2011 |
| WO | WO2012/014164 | 2/2012 |
| WO | WO2012/050938 | 4/2012 |
| WO | WO2012/103073 | 8/2012 |
| WO | WO2012/124328 | 9/2012 |
| WO | WO2012/178171 | 12/2012 |
| WO | WO2013/019749 | 2/2013 |
| WO | WO2013/033669 | 3/2013 |
| WO | WO2013/044226 | 3/2013 |
| WO | WO2013/049658 | 4/2013 |
| WO | WO 2013/146231 A1 | 10/2013 |
| WO | WO2014/109799 | 7/2014 |
| WO | WO2014/194257 | 12/2014 |
| WO | WO 2015/074070 A1 | 5/2015 |
| WO | WO2015/120186 | 8/2015 |
| WO | WO2015/157731 | 10/2015 |
| WO | WO2015/088863 | 12/2015 |
| WO | WO 2016/044251 A1 | 3/2016 |
| WO | WO2016/089466 | 6/2016 |
| WO | WO2017/040669 | 3/2017 |
| WO | WO2017/160751 | 9/2017 |
| WO | WO2018017436 | 1/2018 |

OTHER PUBLICATIONS

U.S. Appl. No. 15/097,744, filed Apr. 13, 2016, Asbeck et al.
U.S. Appl. No. 15/102,694, filed Mar. 31, 2017, De Rossi et al.
U.S. Appl. No. 14/893,934, filed Nov. 24, 2015, Walsh et al.
U.S. Appl. No. 16/538,746, filed Aug. 12, 2019, Asbeck et al.
U.S. Appl. No. 16/317,845, filed Jan. 15, 2019, Ding et al.
U.S. Appl. No. 16/493,746, filed Sep. 12, 2019, Bartlett et al.
U.S. Appl. No. 15/302,347, filed Oct. 6, 2016, Walsh et al.

PCT/US2019/033143, Oct. 9, 2019, International Search Report and Written Opinion.
PCT/US2018/022494, Jun. 8, 2018, International Search Report and Written Opinion.
Banala, S. K. et al., "Active leg exoskeleton (alex) for gait rehabilitation of motor-impaired patients," in Proc. 2007 IEEE 10th Int. Conf. Rehabil Robotics, pp. 401-407, Jun. 2007.
Browning, R. C. et al., "The effects of adding mass to the legs on the energetics and biomechanics of walking," Medicine and Science in Sports and Exercise, col. 39, p. 515, Apr. 2007.
Chu, A. et al, "On the biomimetric design of the Berkeley lower extremity exoskeleton (BLEEX)", Proc. 2005 in IEEE Int. Conf. Robotics and Automation (IEEE Press, Barcelona, Spain, pp. 4356-4363 Apr. 2006).
Clevertex: Development of Strategic Master Plan for the transformation of the traditional textile and clothing into a knowledge driven industrial sector by 2015, 160 pages, dated prior to Jul. 2014.
Collins, S., et al., "Efficient Bipedal Robots Based on Passive-Dynamic Walkers," Science, vol. 307, Issue 5712, pp. 1082-1085, Feb. 18, 2005.
Cool, J.C., "Biomechanics of orthoses for the subluxed shoulder," Prosthetics & Orthotics International; vol. 13, Issue 2, pp. 90-96, 1989.
Da Silva, A. F. et al., "FBG Sensing Glove for Monitoring Hand Posture," IEEE Sensors Journal, vol. 11, Issue 10, pp. 2442-2448, Oct. 2011.
De Rossi, D. et al., "Wearable technology for biomechanics: e-textile or micromechanical sensors?" IEEE engineering in medicine and biology magazine, vol. 29, No. 3, pp. 37-43, May/Jun. 2010. [Online]. Available: http://www.ncbi.nlm.nih.gov/pubmed/20659856.
Delp, S. L. et al., "OpenSim: open-source software to create and analyze dynamic simulations of movement." IEEE transactions on bio-medical engineering, vol. 54, No. 11, pp. 1940-1950, Nov. 2007. [Online]. Available: http://www.ncbi.nlm.nih.gov/pubmed/18018689.
Dollar, A. M. et al., "Lower extremity exoskeletons and active orthoses: Challenges and state-of-the-art", IEEE Transactions on Robotics, vol. 24, No. 1, pp. 144-158, Feb. 2008.
Erk, K. A. et al., "Strain stiffening in synthetic and biopolymer networks," Biomacromolecules, vol. 11, No. 5, pp. 1358-1363, May 2010.
Fams D.J., et al., Human medial gastrocnemius force-velocity behavior shifts with locomotion speed and gait. Proc Natl Acad Sci USA. Jan. 2012; 109:977-982.
Ferris, D. P. et al., "Robotic lower limb exoskeletons using proportional myoelectric control," in EMBC 2009, Annual International Conference of the IEEE Engineering in Medicine and Biology Society, 2009.
Ferris, D.P. et al., A Physiologist's Perspective on Robotic Exoskeletons for Human Locomotion. Int J HR, 4(3): p. 507-528, 2007.
Ghodsi et al., De novo Likelihood-based measures for comparing genome assemblies. In: BMC Research Notes 2013, Aug. 22, 2013—online retrieved on Oct. 25, 2016.
Gibbs, P. et al.: Wearable Conductive Fiber Sensors for Multi-Axis Human Joint Angle Measurements. Journal of NeuroEngineeiing and Rehabilitation, Mar. 2, 2005.
Goodvin, C.I.: Development of a Real-time Spinal Motion Inertial Measurement System for Vestibular Disorder Application, University of Victoria, 155 pages, date 2003.
Gregorczyk, K. N., et al., The effects of a lower body exoskeleton load carriage assistive device on oxygen consumption and kinematics during walking with loads, in 25th Army Sci. Conf., Florida, USA, 2006.
Hallemans, A. et al.: 3D joint dynamics of walking in toddlers. A cross-sectional study spanning the first rapid development phase of walking. Gait & Posture, 22:107-118, 2005.
Kadaba, M. P., et al., "Measurement of lower extremity kinematics during level walking." Journal of orthopaedic research: official publication of the Orthopaedic Research Society, vol. 8, No. 3, pp. 383-392, May 1990. [Online]. Available: http://www.ncbi.nlm.nih.gov/pubmed/2324857.

(56) References Cited

OTHER PUBLICATIONS

Kawamoto, H., et al., Power assist method for HAL-3 using EMG-based feedback controller. in Systems, Man and Cybernetics, 2003. IEEE International Conference on. 2003.
Kim, D.-H. et al., "Epidermal electronics." Science, vol. 333, No. 6044, pp. 838-843, Aug. 2011. [Online] Available: http://www.sciencemag.org/cgi/doi/10.1126/science.1206157.
Kramer, R. K. et al., "Soft curvature sensors for joint angle proprioception," in 2011 IEEE/RSJ International Conference on Intelligent Robots and Systems. IEEE, pp. 1919-1926, Sep. 2011. [Online]. Available: http://ieeexplore.ieee.org/lpdocs/epic03/wrapper.htm?arnumber=6094701.
Kramer, R. K. et al., "Wearable tactile keypad with stretchable artificial skin," 2011 IEEE International Conference on Robotics and Automation, pp. 1103-1107, May 2011. [Online]. Available: http://ieeexplore.ieee.org/lpdocs/epic03/wrapper.htm?arnumber=5980082.
Kulyukin, V. A.: Advances in Human-Robot Interaction, 354 pages, Dec. 2009.
Lee, S. W. et al.: Biomimetic Approach Enables Functional Movements of Hand Post Stroke: A Pilot Study, 2 pages, dated 2012.
Lipomi, D. J. et al., "Skin-like pressure and strain sensors based on transparent elastic films of carbon nanotubes." Nature nanotechnology, vol. 6, No. 12, pp. 788-792, Jan. 2011. [Online]. Available: http://www.ncbi.nlm.nih.gov/pubmed/22020121.
Majidi, C. et al., "A non-differential elastomer curvature sensor for softer-than-skin electronics," Smart Materials and Structures, vol. 20, No. 10, p. 105017, Oct. 2011. [Online]. Available: http://stacks.iop.org/0964-1726/20/i=10/a=105017?key=crossref.0cca7e97d6ad7110bcdcaf45f30f3b60.
Malcolm, Philippe et al., Fast Exoskeleton Optimization. Science, vol. 356, Issue 6344, pp. 1230-1231, Jun. 23, 2017.
Mattila, H. R., Intelligent textiles and clothing, Woodhead Publishing Limited, 525 pages, © 2006.
McGeer, T., Passive Bipedal Running. Proceedings of the Royal Society of London. Series B, Biological Sciences, 240(1297): p. 107-134, May 1990.
Newman, D. J. et al., Astronaut Bio-Suit System to Enable Planetary Exploration. In International Astronautical Conference, Vancouver, Canada, Oct. 2004.
Park, Y. L. et al., Active Modular Elastomer Sleeve for Soft Wearable Assistance Robots, 2012 IEEE/RSJ International Con. On Intelligent Robots and Systems Vilamoura, Algarve, Portugal, 8 pages, Oct. 7-12, 2012.
Park, Y.-L., et al., "Design and Fabrication of Soft Aitificial Skin Using Embedded Microchannels and Liquid Conductors," IEEE Sensors Journal, vol. 12, No. 8, pp. 2711-2718, Aug. 2012. [Online]. Available: http://ieeexplore.ieee.org/lpdocs/epic03/wrapper.htm?arnumber-6203551.
Park, Y.-L., "Hyperelastic pressure sensing with a liquid-embedded elastomer," Journal of Micromechanics and Microengineering, vol. 20, No. 12, p. 125029, Dec. 2010. [Online]. Available: http://stacks.iop.org/0960-1317/20/i=12/a=1250297key=crossref.84cffc44789ba7bde0bdfd169e25af91.
Park, Y.-L., et al.: Bio-inspired Active Soft Orthotic Device for Ankle Foot Pathologies, 2011 IEEE/RSJ International Conference on Intelligent Robots and Systems, San Francisco, CA, USA, 8 pages, Sep. 25-30, 2011.
Pereira da Fonseca, P. F.: Validation of two types of textile electrodes for electrocardiography and electromyography measurement applications, 126 pages, dated Jul. 2012.
Polonen et al. Automatic Intensity Quantification of Fluorescence Targets from microscope Images with Maximum Likelihood Estimation. 17th Emopean Signal Processing Conference, Aug. 24-28, 2009—retrieved online Oct. 25, 2016.
Pratt, J. et al., The RoboKnee: An exoskeleton for enhancing strength and endurance during walking, in IEEE Int. Conf. Robotics and Automation (ICRA), New Orleans, USA (IEEE Press), pp. 2430-2435, Apr. 2004.

Quintero, H. A. et al., "Control and Implementation of a Powered Lower Limb Orthosis to Aid Walking in Paraplegic Individuals," in IEEE International Conference on Rehabilitation Robotics, Switzerland, pp. 1-6, Jun. 29-Jul. 1, 2011.
Ramuz, M. et al., "Transparent, Optical, Pressure-Sensitive Artificial Skin for Large-Area Stretchable Electronics," Advanced Materials, May 2012. [Online]. Available: http://doi.wiley.com/10.1002/adma.201200523.
Reid, S. A. et al., "Biomechanical assessment of rucksack shoulder strap attachment location: effect on load distribution to the torso," presented at the RTO HFM specialists' Meeting on "Soldier Mobility: Innovations in Load Carriage System Design and Evaluation," NATO-RTO Meeting Proceedings: MP-056 (Neuilly-sur-Seine: NATO). 1-6, Jun. 2000.
Royer, T.D. et al., (2005) Manipulations of Leg Mass and Moment of Inertia: Effects onEnergy Cost of Walking, Medicine & Science in Sports & Exercise, vol. 37. No. 4: p. 649-656, 2005.
Salvendy, G.: Smart Clothing Technology and Applications, Human Factors and Ergonomics, by Taylor and Francis Group, LLC, 290 pages, © 2010.
Schiele, A. "Ergonomics of Exoskeletons: Objective Performance Metrics" in Euro Haptics conference and symposium on Haptic Interfaces for Virtual Environmental Teleoperator Systems, Salt Lake City, UT, USA, Mar. 2009.
Scilingo, E. P. et al., "Strain-sensing fabrics for wearable kinaesthetic-like systems," IEEE Sensors Journal, vol. 3, No. 4, pp. 460-467, Aug. 2003. [Online]. Available: http://ieeexplore.ieee.org/lpdocs/epic03/wrapper.htm?arnumber=1226639.
Silva, H. R., et al.: Wireless Hydrotherapy Smart-Suit Network for Posture Monitoring, 5 pages, dated 2007.
Strauser, K. A. et al., "The development and testing of a human machine interface for a mobile medical exoskeleton" in IEEE Int Conf, Intelligent Robots and Systems, San Francisco, CA. USA, Sep. 2011.
Tesconi, M., et al., "Wearable sensorized system for analyzing the lower limb movement during rowing activity," 2007 IEEE International Symposium on Industrial Electronics, pp. 2793-2796, Jun. 2007. [Online]. Available: http://ieeexplore.ieee.org/lpdocs/epic03/wrapper.htm?arnumber=4375052.
Tiwana, M. I., et al., "A review of tactile sensing technologies with applications in biomedical engineering," Sensors and Actuators A: Physical, vol. 179, pp. 17-31, Jun. 2012. [Online]. Available: http://linkinghub.elsevier.com/retrieve/pii/S0924424712001641.
Vogt, D. M., et al., Design and Characterization of a Soft Multi-Axis Force Sensor Using Embedded Microfludic Channels, IEEE Sensors Journal, vol. 13. No. 10, 9 pages, Oct. 2013.
Walsh, C. J., et al., A Quasi-Passive Leg Exoskeleton for Load Carrying Augmentation. International Journal of Humanoid Robotics, Special Issue: Active Exoskeletons, 4(3): 487-506, 2007.
Wehner, M., 2012 "Manto Machine, Applications in Electromyography," EMG Methods for Evaluation Muscle and Nerve Functions. Intech Publishing, Sep. 13, 2012 http://intechopen.com/articles/show/title/man-to-machine-applications-in-electromyography.
Wehner, M., et al., "Experimental characterization of components for active soft orthotics," in Proc. IEEE Int. Conf. Biomed. Rob. Biomechatron., Roma, Italy, Jun. 2012.
Wehner, M., et al., "Lower Extremity Exoskeleton Reduces Back Forces in Lifting" ASME Dynamic Systems and Control Conference, Hollywood, California, USA pp. 49-56, Oct. 12-14, 2009.
Woodman, O.J. "An introduction to inertial navigation," Technical Report UCAM-CL-TR-696, Aug. 2007.
Yamada, T. et al., "A stretchable carbon nanotube strain sensor for human-motion detection." Nature Nanotechnology, vol. 6, No. 5 pp. 296-301, May 2011. [Online]. Available: http://ncbi.nlm.nih.gov/pubmed/21441912.
Zhang, R. et al., "Carbon nanotube polymer coatings for textile yams with good strain sensing capability," Sensors and Actuators A: Physical, vol. 179, pp. 83-91, Jun. 2012. [Online]. Available: http://linkinghub.elsevier.com/retrieve/pii/S0924424712001938.
Zhang, Juanjuan et al., Human-in-the-Loop Optimization of Exoskeleton Assistance During Walking, Science, vol. 356, pp. 1280-1284, Jun. 23, 2017.

(56) References Cited

OTHER PUBLICATIONS

Zoss, A.B., et al., Biomechanical design of the Berkeley lower extremity exoskeleton (BLEEX), IEE/ASME Transactions on Mechatronics, 11(2): p. 128-138, Apr. 2006.
PCT International Search Report, issued in International Application No. PCT/EP2003/012123, dated Jun. 22, 2004.
PCT International Search Report and Written Opinion, issued in International Application No. PCT/US2013/060225, dated May 27, 2014.
PCT International Search Report and Written Opinion, issued in International Application No. PCT/US2014/040340, dated Oct. 31, 2014,.
PCT International Search Report and Written Opinion, issued in International Application No. PCT/US2014/068462, dated May 22, 2015.
PCT International Search Report and Written Opinion, issued in International Application No. PCT/US2015/014672, dated Jul. 6, 2015.
PCT International Search Report and Written Opinion, issued in International Application No. PCT/US2015/025472, dated Sep. 4, 2015.
PCT International Search Report and Written Opinion, issued in International Application No. PCT/US2015/051107 dated Aug. 5, 2016.
Extended European Search Report issued in European Application No. 13871010.8 dated Sep. 2, 2016.
PCT International Search Report and Written Opinion, issued in International Application No. PCT/US2016/049706 dated Nov. 29, 2016.
Extended European Search Report issued in European Application No. 14803880.5 dated May 19, 2017.
PCT International Search Report and Written Opinion, issued in International Application No. PCT/US2017/042286, dated Sep. 28, 2017.
Supplementary European Search Report issued in European U.S. Appl. No. 15/776,544 dated Oct. 20, 2017.
USPTO Office Action in U.S. Appl. No. 14/660,704 dated Feb. 7, 2018.
Extended European Search Report issued in European Application No. 15746146.8 dated Feb. 27, 2018.
USPTO Office Action in U.S. Appl. No. 14/660,704 dated Jun. 28, 2018.
USPTO Office Action in U.S. Appl. No. 15/117,034 dated Oct. 5, 2018.
USPTO Office Action in U.S. Appl. No. 14/660,704 dated Nov. 8, 2018.
International Search Report and Written Opinion for International Application No. PCT/US2019/033143, dated Oct. 9, 2019.
International Search Report and Written Opinion for International Application No. PCT/US2018/022494, dated Jun. 8, 2018.
Bae et al, A Soft Exosuit for Patients with Stroke: Feasibility study with a mobile off-board actuation unit. 2015 IEEE International Conference on Rehabilitation Robotics (ICORR). Aug. 11, 2015; 131-8.
Laughton et al., Effect of Strike Pattern and Orthotic Intervention on Tibial Shock During Running. Journal of Applied Biomechanics. May 1, 2003; 19(2): 153-68.
Lenhart et al., Increasing Running Step Rate Reduces Patellofemoral Joint Forces. Medicine & Science in Sports & Exercise. Mar. 2014; 46(3): 557-64.
Lieberman et al., Effects of stride frequency and foot position in landing on braking force, hip torque, impact peak force and the metabolic cost of running in humans. Journal of Experimental Biology. Nov. 1, 2015; 218(21):3406-14.
Sinclair et al., Determination of Gait Events Using an Externally Mounted Shank Accelerometer. Journal of Applied Biomechanics. Feb. 1, 2013; 29(1): 118-22.

\* cited by examiner

FLEXIBLE MEMBERS FOR ANCHORING TO THE BODY

CROSS-REFERENCE AND CLAIM OF PRIORITY TO RELATED APPLICATIONS

This application is a U.S. national phase application of PCT International Patent Application No. PCT/US2017/022150, filed on Mar. 13, 2017, which claims the benefit of and priority to U.S. Provisional Patent Application No. 62/307,545, filed Mar. 13, 2016, the entirety of each of which is hereby incorporated by reference.

STATEMENT REGARDING FEDERALLY SPONSORED RESEARCH OR DEVELOPMENT

At least some of the aspects of the presently disclosed embodiments were made with government support from the Defense Advanced Research Projects Agency (DARPA), under Grant W911NF-14-00051. The government shares rights to such aspects of the invention.

FIELD

The presently disclosed embodiments relate to wearable systems and devices, and more particularly, to flexible members for comfortably and securely anchoring components of wearable systems and devices to the body.

BACKGROUND

Many exosuits, joint braces, and other wearable systems and devices configured for supporting and/or assisting motion of the body face challenges in terms of both securely and comfortably interfacing with the body. Flexible materials are often used so as to not inhibit natural motion of the body; however, it can be difficult to securely anchor such materials to body parts without the constant use of uncomfortably high levels of compressive forces. Natural motion of the body, as well as cyclical relaxation and contraction of underlying musculature, often causes such wearable systems and devices to migrate from desired positions on the body, which can reduce effectiveness and cause wearer discomfort and annoyance. Further, applied forces such as those generated by an actuator or passive element (e.g., a spring), may cause migration as well as potentially deform (e.g., scrunch up or stretch) flexible materials used in these wearable systems. According, an improved design is needed for both comfortably and securely engaging the body with wearable systems and devices.

SUMMARY

The present disclosure is directed to flexible anchor members configured to comfortably engage the body of a wearer while resisting forces that may otherwise cause migration of the flexible anchor member on the body.

A flexible anchor member of the present disclosure may include a member for placement about a body part of a wearer, at least one substantially inextensible textile element partially or fully circumscribing the member and configured in one or more locations to be secured to itself or to the member, and a force transfer coupler configured to couple a portion of the at least one substantially inextensible textile element to an actuator such that a force applied by the actuator causes the at least one substantially inextensible textile element to constrict about the member for a duration of the applied force.

The member, in some embodiments, may be substantially planar and may include one or more fasteners for securing the member about the body part, while in other embodiments, the member may be substantially cylindrical or conical and configured to be pulled onto or rolled onto the body part. The member may include a mechanism for adjustably applying a pre-compression force about the body part. The member, in various embodiments, may further include at least one stiffening element for enhancing a longitudinal stiffness of the member. The force transfer coupler, in some such embodiments, may couple an actuator to a central portion of the member or to an end of the member situated closest to the actuator.

In various embodiments, constriction of the at least one substantially inextensible textile element about the member may generate a compression force that acts on the member to resist migration of the member for the duration of the applied force. The flexible anchor member may further include one or more fasteners for securing the at least one substantially inextensible textile element to itself or to the member. The one or more fasteners, in some embodiments, may be further configured for adjusting a length of the at least one substantially inextensible textile element available for constricting about the member in response to the applied force.

The force transfer coupler, in various embodiments, may also be coupled to the member and configured to transfer a first portion of the applied force to the member and a second portion of the applied force to the at least one substantially inextensible textile element. In some such embodiments, the flexible anchor member may further include one or more fasteners for securing the at least one substantially inextensible textile element to the member and for adjusting a path followed by the at least one substantially inextensible textile element about the member, thereby adjusting an amount of friction generated between the at least one substantially inextensible textile element and the member as the at least one substantially inextensible textile element constricts about the member. The one or more fasteners, some embodiments, may be configured for adjusting a ratio of the first portion of the applied force transferred to the member and the second portion of the applied force transferred to the at least one substantially inextensible textile element.

The flexible anchor member, in some embodiments, may further include a substantially inextensible textile material configured for directing a force applied by an actuator to act upon all or a portion of the body part. In various embodiments, the flexible anchor member may further include at least one of an electrode, a sensor, and wiring embedded within or otherwise integrated into the member.

Another flexible anchor member of the present disclosure may include an outer member for placement about a body part, an inner member for positioning between the body part and the outer member, and at least one coupler for coupling the outer member and the inner member.

The outer member may include a substantially inextensible textile material configured for directing a force applied by an actuator to act upon all or a portion of the body part. In an embodiment, all or most of the outer member may be made from the substantially inextensible textile material and the substantially inextensible textile material may be configured for directing the applied force substantially circumferentially around the underlying body part. In another embodiment, the substantially inextensible textile material may extend between a first location and a second location of the outer member so as to direct the applied force from the first location to the second location. The second location, in an embodiment, may be associated with at least one of a bony anatomical feature of the body part and a portion of the body part having resilient tissue or muscle.

A first surface of the inner member may be configured for frictionally engaging the body part or any intervening clothing. The inner member, in various embodiments, may act to resist migration of the outer member relative to the body part in response to one or a combination of the applied force and natural motion of the body part.

The at least one coupler, in some embodiments, may be configured for selectably coupling and decoupling the outer member and the inner member. Representative embodiments of such a coupler may include a hook and loop fastener, a snap, a button, and a zipper. In other embodiments, the at least one coupler may fixedly couple the outer member and the inner member. Representative embodiments of such a coupler may include sewn seams, adhesive, rivets, and a heat bond. In various embodiments, at least one of the outer member and the inner member may be substantially planar and include one or more fasteners for forming into a substantially cylindrical or conical shape. At least one of the outer member and the inner member, in some embodiments, may be configured to be pulled onto or rolled onto the body part.

The outer member, in various embodiments, may include a mechanism for adjustably applying a pre-compression force about the body part. The outer member, in various embodiments, may further include at least one stiffening element for enhancing a longitudinal stiffness of the outer member. In some such embodiments, the outer member may be configured to couple to the actuator at a central portion of the outer member or at an end of the outer member situated closest to the actuator.

The first surface of the inner member, in various embodiments, may include an anti-slip material for enhancing a coefficient of friction of the first surface of the inner member. Representative embodiments of the anti-slip material may include at least one of a polyurethane-coated fabric, a polyurethane-polyester blend material, silicone, and adhesive.

The inner member, in various embodiments, may further include a second surface and a thickness between the first surface and the second surface. The thickness of the inner member may vary along at least a portion of the inner member such that a shape of the first surface complements a specific geometry of the body part. In an embodiment, the inner member may be configured for use with a calf of the wearer, and may be thicker in an area configured for placement against a belly of the calf muscle and thinner in an area configured for placement against the tibial tuberosity.

An elastic modulus of the inner member, in various embodiments, may vary along at least a portion of the inner member. Variations in the elastic modulus, in some embodiments, may be configured to distribute, uniformly onto the body part, a force applied to the inner member by the outer member. In other embodiments, variations in the elastic modulus may be configured to direct, onto a specific portion of the body part, a force applied to the inner member by the outer member.

The flexible anchor member, in various embodiments, may further include a second inner member for positioning between the body part and the outer member. The second inner member may have a shape substantially similar to the first inner member such that the inner member and the second inner member may be selectively interchanged for use with the outer member. In some embodiments, the inner member may be configured to complement a specific geometry of the body part at a first stage of a physical rehabilitation program or a training program, and the second inner member may be configured to complement a specific geometry of the body part at a second stage of the physical rehabilitation program or the training program. In other embodiments, the inner member may be configured to complement a specific geometry of the body part of a first person, and the second inner member may be configured to complement a specific geometry of the body part of a second person.

The flexible anchor member, in various embodiments, may further include at least one of an electrode, a sensor, and wiring embedded within or otherwise integrated into at least one of the outer member and the inner member. In an embodiment, both the inner member and the outer member include at least one electrode, sensor, and/or wiring embedded within or otherwise integrated therein, and the at least one coupler provides an electrical connection between the electronics of the inner member and the electronics of the outer member.

The flexible anchor member, in an embodiment, may further include at least one substantially inextensible textile element partially or fully circumscribing a portion or all of the outer member and configured in one or more locations to be secured to itself or to the outer member. A portion of the at least one substantially inextensible textile element may be configured to be coupled to an actuator such that a force applied by the actuator causes the at least one substantially inextensible textile element to constrict about the outer member for a duration of the applied force.

BRIEF DESCRIPTION OF DRAWINGS

The presently disclosed embodiments will be further explained with reference to the attached drawings, wherein like structures are referred to by like numerals throughout the several views. The drawings shown are not necessarily to scale, with emphasis instead generally being placed upon illustrating the principles of the presently disclosed embodiments.

While the above-identified drawings set forth presently disclosed embodiments, other embodiments are also contemplated, as noted in the discussion. This disclosure presents illustrative embodiments by way of representation and not limitation. Numerous other modifications and embodiments can be devised by those skilled in the art which fall within the scope and spirit of the principles of the presently disclosed embodiments.

DETAILED DESCRIPTION

Embodiments of the present disclosure are directed to flexible anchor members 100 configured to provide extremely secure and comfortable anchoring to various parts of a wearer's body. For example, embodiments of flexible anchor member 100 may be adapted for anchoring to parts of the wearer's lower body or legs (e.g., the waist, thigh, calf, foot), as well as to parts of the wearer's upper body (e.g., the torso, upper arm, forearm, hand).

Features of flexible anchor member 100 act to resist forces that may otherwise cause flexible anchor member to migrate relative to the underlying body part. As described in more detail below, flexible anchor member 100, in various embodiments, may be configured to apply any one or combination of frictional, pre-compression, and dynamic compression forces on the body part to resist natural and applied forces, thereby enhancing anchoring to the body part while maintaining user comfort. As configured, embodiments of flexible anchor member 100 may be suitable for use with actuated wearable systems such as exosuit 10 described below, as well as with other wearable robotic devices for assisting with movement, training, recovery or rehabilitation. Embodiments of flexible anchor member 100 may be further suitable for use with non-actuated devices such as braces for athletic, medical, industrial, and ergonomic applications.

Exosuit 10

Figure 1C:
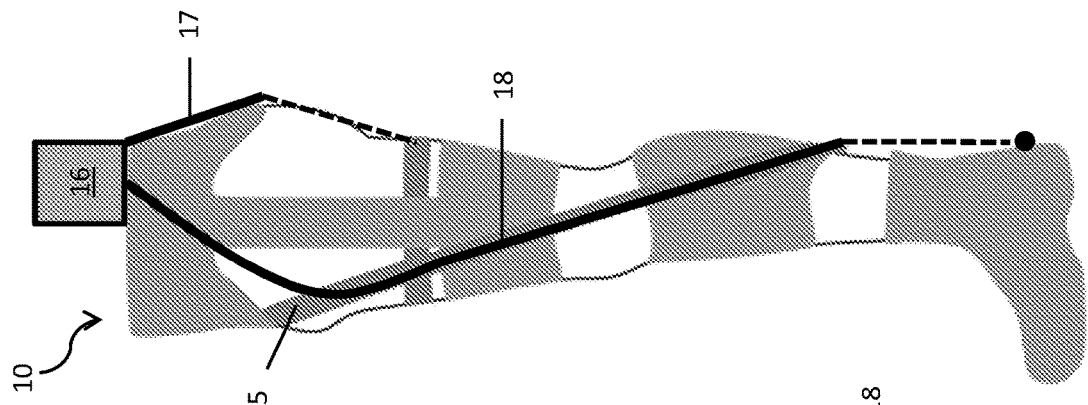
FIG. 1A, FIG. 1B, and FIG. 1C show front, rear, and side views of a representative soft exosuit.
Figure 1B:
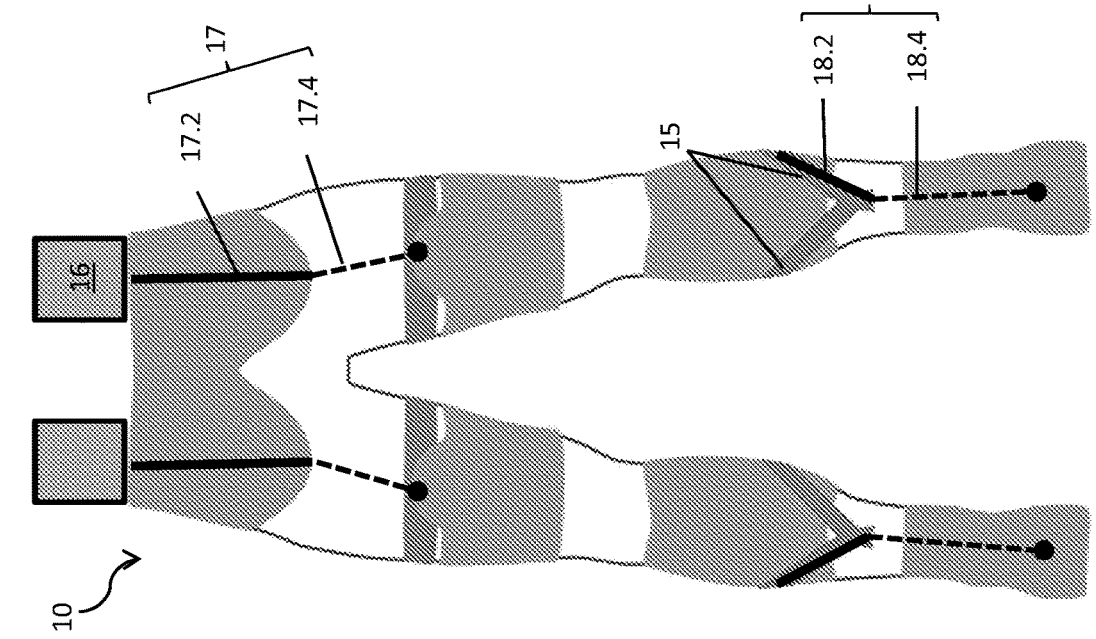
Figure 1A:
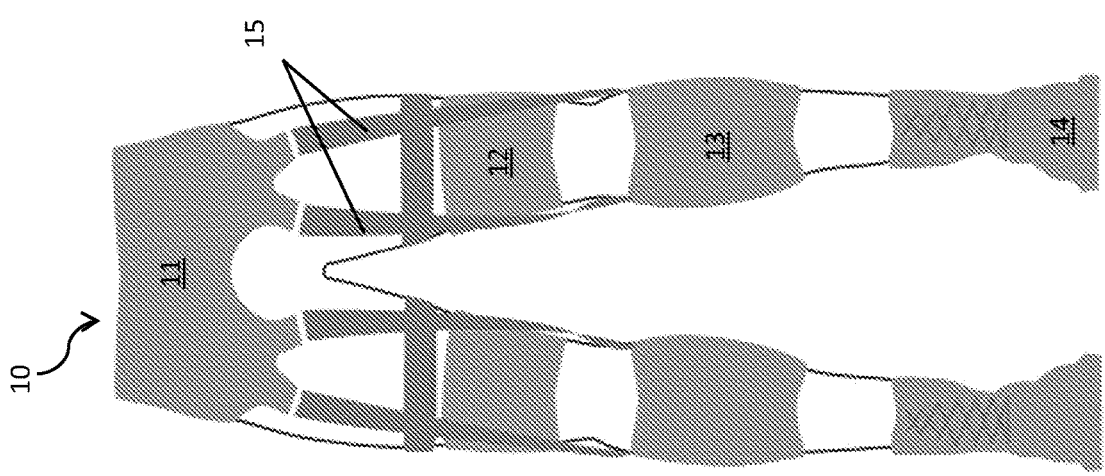

FIG. 1A, FIG. 1B, and FIG. 1C illustrate front, rear, and side views, respectively, of a representative soft exosuit 10. In various embodiments, exosuit 10 may include a waist anchor member 11, a thigh anchor member 12, a calf anchor member 13, a foot anchor member 14, connection elements 150, actuators 16, and actuation members 17, 18.

Anchor members 11, 12, 13, and 14 are designed to engage corresponding body parts of the wearer of exosuit 10 and act to resist forces applied by actuator 16. As configured, exosuit 10 may be configured to apply moments about one or more body joints of the wearer. In some embodiments, the generation of these moments may be timed such that the exosuit 10 provides a boost of power for assisting or encouraging natural body motions. Additionally or alternatively, exosuit 10 may passively apply moments for similar purposes.

Actuator 16 may apply tensile forces to portions of exosuit 10 via actuation members 17, 18, shown here as Bowden cables, having sheaths 17.2, 18.2 and inner cables 17.4, 18.4. Such a construction allows actuation members 17, 18 to deliver tensile force to a portion of exosuit 10 distal from actuator 16, without necessarily applying the tensile force to intermediate portions of exosuit 10. In particular, a distal end of sheath 18.2 may be coupled with calf anchor 13 and a distal end of inner cable 18.4 coupled with foot anchor 14, such that when inner cable 18.4 is pulled by actuator 16, the tensile force is applied to the lower portion of exosuit 10.

Connection elements 15 may extend between some of the anchors and may act as conduits through which tensile forces applied to one part of exosuit 10 may be transferred to other parts of exosuit 10. In this way, exosuit 10 may direct the tensile force along pathways suitable for generating desired moments about one or more body joints of the wearer. Such a configuration may also be used to distribute an applied tensile force amongst multiple body parts, thereby improving comfort and increasing the magnitude of force that may be applied to assist or encourage motion. Connection elements 15 of this particular representative embodiment may extend between waist anchor 11 and calf anchor 13, and in particular, are routed down the front of the thigh, around the side of the knees, and around the back of the calf, where they couple with calf anchor 13 and actuation member 18. Tensile forces applied to the lower portion of exosuit 10 by actuation member 18 may be directed upward through connection elements 15 towards waist anchor 11. Such a configuration may be used to generate desired moments about any one or combination of the ankle, knee, and hip joints of the wearer, from just one actuation input.

Flexible Anchor Member 100

Figure 2:
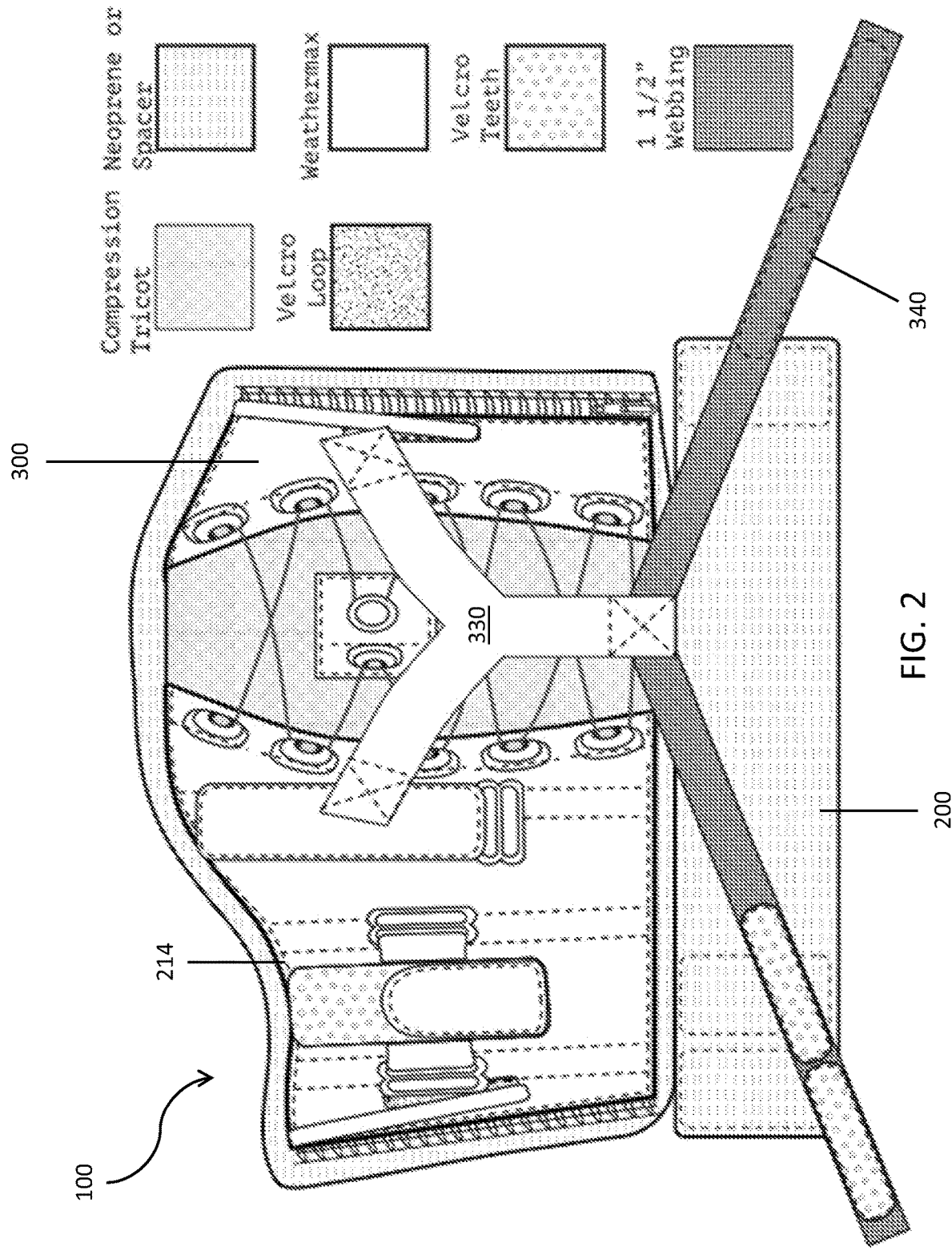
FIG. 2 shows an inner member and an outer member of a flexible anchor member, in accordance with an embodiment of the present disclosure.

FIG. 2 depicts a representative embodiment of a flexible anchor member 100 including an inner member 200 and an outer member 300.

Inner member 200 may be positioned between the body part and outer member 300 and have a first surface configured for frictionally engaging the body part or any intervening clothing. As configured, inner member 200 may act to resist migration of outer member 300 relative to the body part in response to one or a combination of an applied force (e.g., a tensile force applied by actuator 16 of exosuit 100) and natural motion of the body part. In some embodiments, at least one coupler 216 may fixedly couple inner member 200 to outer member 300 (shown here as a stitched seam), while in other embodiments, at least one coupler 214 may be configured for selectably coupling and decoupling inner member 200 and outer member 300, as later described in more detail. Inner member 200, in various embodiments, may be further configured to distribute forces transferred from outer member 300 uniformly onto the body part or to direct these forces onto a specific portion or portions of the body part, thereby enhancing wearer comfort, as later described in more detail.

Outer member 300 may be positioned about inner member 200 and the body part. Outer member 300, in various embodiments, may be configured to tighten about the body part via a tensioning or adjustment mechanism to apply a level of pre-compression to the body for improving anchoring. The term "pre-compression" is used to describe a normal force continuously applied to the underlying body by outer member 300.

In various embodiments, outer member 300 may include a substantially inextensible textile material configured for directing a force applied by an actuator to act upon one or more portions of the body part, as later described in more detail. Additionally or alternatively, in some embodiments, outer member 300 may include an substantially inextensible textile element 340 (e.g., a textile strap) configured to create a dynamic compression force on the body part. The term "dynamic compression" is used to describe a temporary compressive force generated by the constriction of substantially inextensible textile element 340 in response to an applied force, such as one generated by actuator 16 or exosuit 10. In particular, and as described in more detail below, a force transfer coupler 330 may couple a portion of the at least one substantially inextensible textile element 340 to a source of the applied force such that the applied force causes the at least one substantially inextensible textile element 340 to constrict about outer member 300 for a duration of the applied force, thereby generating a dynamic compression force for enhancing anchoring of flexible anchor member 100 to the body part. The substantially inextensible textile element may be integrated into a body section of outer member 300 in some embodiments, while in other embodiments it may be a separate component coupled thereto.

While the representative embodiment of flexible anchor member 100 includes both inner member 200 and outer member 300, in some embodiments, outer member 300 may be used independent of inner member 200 in other embodiments. Stated otherwise, flexible anchor member 100 may include only outer member 300 in some embodiments. Various other embodiments of flexible anchor member 100 may include any one or combination of suitable features drawn from inner member 200 and outer member 300.

Inner Member 200

Figure 3:
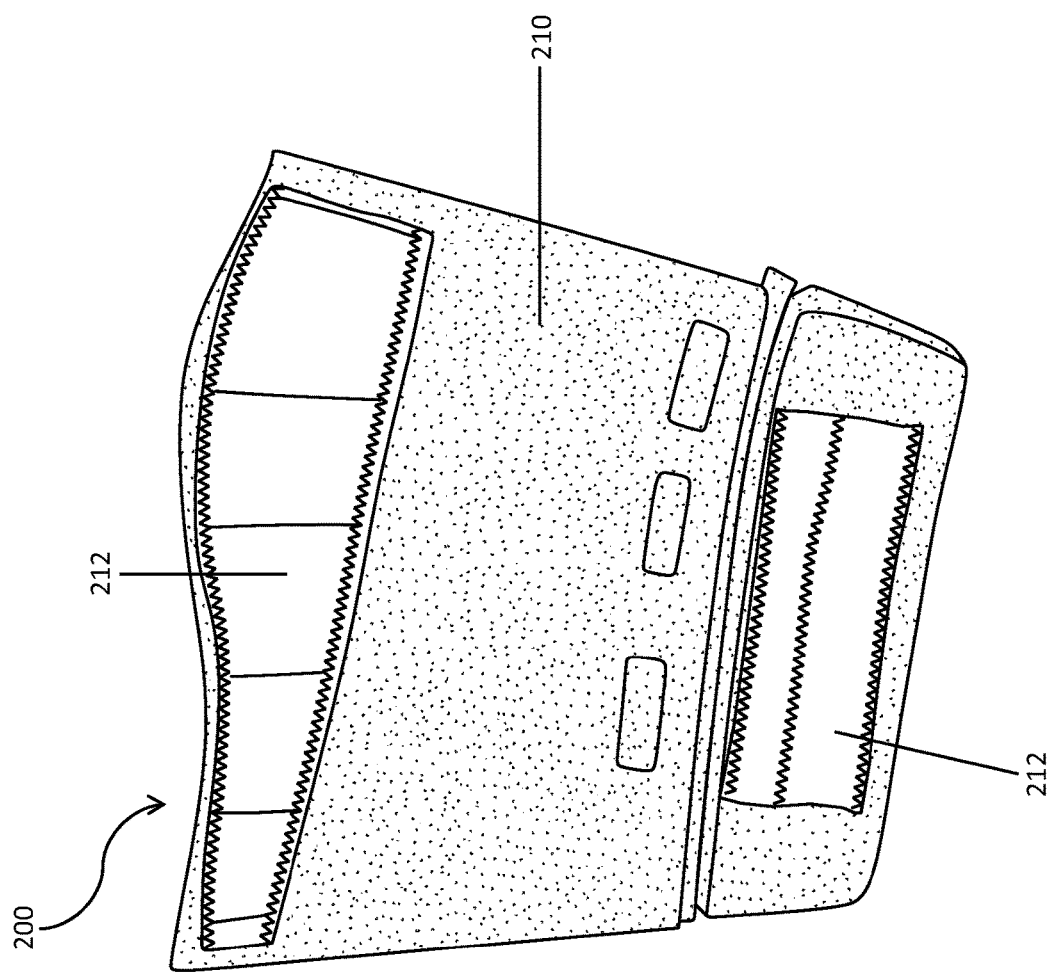
FIG. 3 shows an inner member of a flexible anchor member, in accordance with an embodiment of the present disclosure.

FIG. 3 depicts a representative embodiment of inner member 200 of flexible anchor member 100. Embodiments of inner member 200 may have constructions suitable for at least one of:

1) Distributing pre-compression and/or applied forces transferred from outer member 300 to minimize pressure points on underlying bodily tissues, thus reducing risk of injury and enhancing comfort, and/or
2) Improving the interface of flexible anchor member 100 with the wearer's body, in terms of frictionally engaging the body part for preventing migration of flexible anchor member 100, and also in terms of sweat wicking or breathability.

Figure 5:
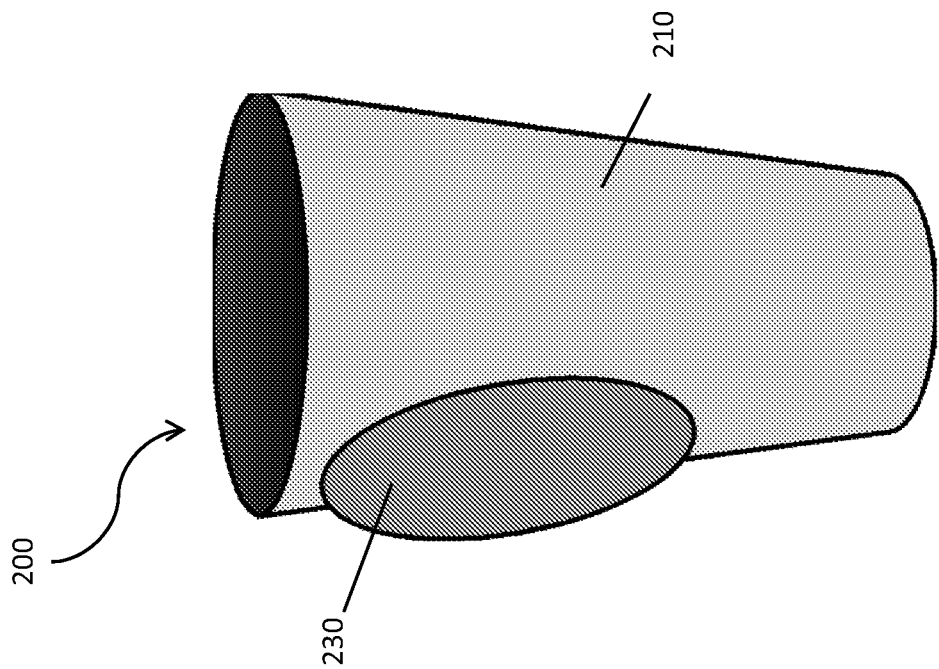
FIG. 5 shows an inner member of a flexible anchor member, in accordance with yet another embodiment of the present disclosure.
Figure 4:
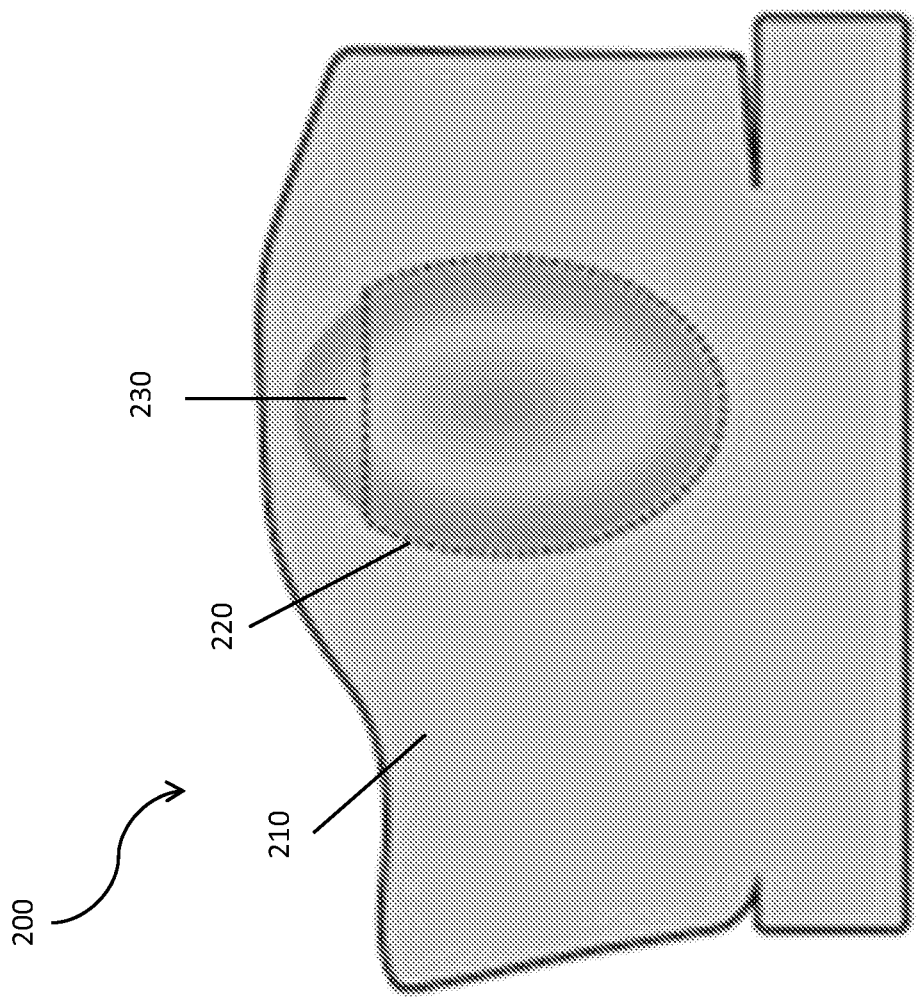
FIG. 4 shows an inner member of a flexible anchor member, in accordance with another embodiment of the present disclosure.

Body section 210 of inner member 200, in various embodiments, may be configured to wrap around, slide onto, or otherwise engage a body part of the wearer. In the embodiment shown in FIG. 3, inner member 200 is flat and wraps around the body part, where opposing edges are joined together by any suitable fastener known in the art. If outer member 300 is longer than a circumference of the underlying body part (or inner member 200), the edge portions of outer member 300 may overlap and fasteners used to secure outer member 300 in this configuration. FIG. 4 shows a flat inner member with a pocket for inserting pre-formed shaped insert. FIG. 5 shows an inner member 200 that is cylindrical and the inner member has variable thickness properties. In the embodiment of FIG. 5, inner member 200 may have a closed, sleeve-style shape (e.g., cylindrical, conical, etc.) and is configured to be pulled onto or rolled onto the body part to which it will be anchored. In some embodiments, conical-shaped sleeves may be preferred, as the tapered shape may resist slippage of the sleeve in the direction of the larger end by mechanically locking with the underlying musculature and/or skeletal structure. Since it may be difficult to pull on sleeve-like embodiments having an anti-slip inner surface, wearers may choose to roll on such sleeve-like inner members, starting with the anti-slip side facing outward and upside down (in the case where the entire inner surface is coated with anti-slip material), or else by folding the top edge over to keep the anti-slip material facing outward until it is correctly positioned and can be folded back so that the anti-slip surface is in contact with the wearer (in the case where only the top portion of the inner member's inner surface is coated with anti-slip material).

It should be recognized that, in some cases, embodiments of inner member 200 fabricated with a closed shape may reduce the potential for skin irritation that may otherwise be caused by overlapping edges at the joinder of edges in flat embodiments. Of course, flat constructions may be designed to minimize or obviate any such potential.

In various embodiments, body section 210 may be made from any textile or similar material having sufficient flexibility for accommodating flexing and other movements associated with the tissue, underlying muscles, joints, etc. of the body part, while still having sufficient shear strength to resist significant deformation under loads applied thereto during actuation of the exosuit. Example materials include, without limitation, neoprene, open or closed cell foam, or mesh spacers, amongst other suitable materials or combinations thereof. Sweat and temperature management may be of concern when dealing with long term wear of inner member 210. For this reason, we present another embodiment of the inner member with a breathable mesh spacer to reduce incidence of sweating. Inner member may additionally or alternatively include other breathable, perforated, or sweat-wicking materials and constructions for this purpose as well.

Figure 14A:
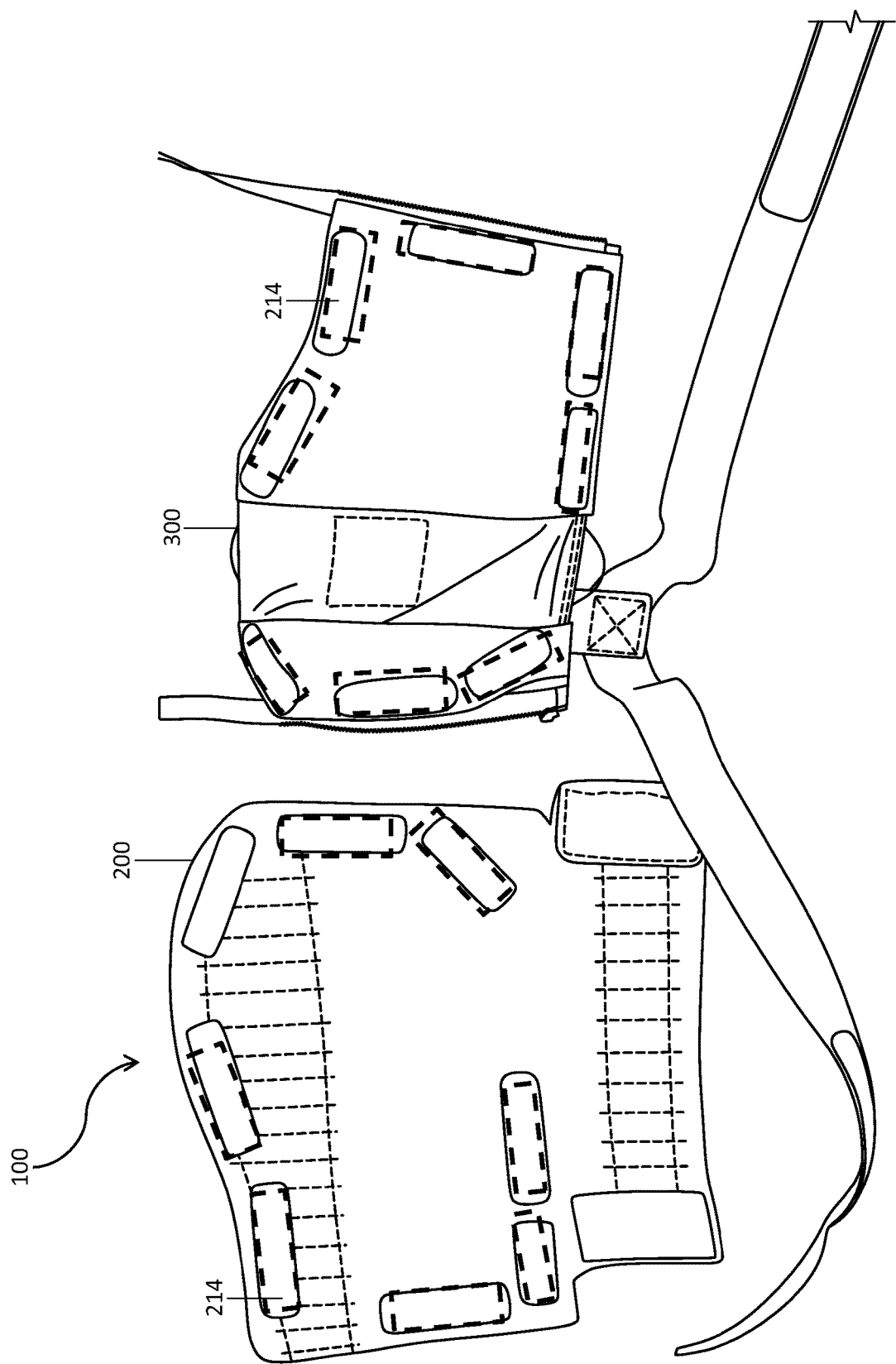
FIG. 14A, FIG. 14B, FIG. 14C, FIG. 14D, FIG. 14E, FIG. 14F, FIG. 14G, FIG. 14H, FIG. 14I, and FIG. 14J show a step-by-step method of donning a flexible anchor member, in accordance with an embodiment of the present disclosure.

In some embodiments, inner member 200 may passively interface with outer member 300. In still other embodiments, inner member 200 and outer member 300 may be fixedly coupled to one another by at least one coupler 216 (not shown), such as, without limitation, sewn seams, rivets, adhesive, or a heat bond. As configured, inner member 200 and outer member 300 are not easily detached from one another, but rather form a substantially unitary article. In still other embodiments, as shown in FIG. 14A, flexible anchor member 100 may include at least one coupler 214 for selectably coupling and decoupling inner member 200 and outer member 300. Representative embodiments of coupler 214 include, without limitation, hook and loop fasteners (e.g., Velcro), snaps, buttons, and zippers. As configured, inner member 200 can be easily removed from the outer member, and may be hand- or machine-washable. FIG. 14A shows multiple strips of Velcro positioned about a perimeter of both outer member 300 and inner member 200 such that the male strips on one member complement the positioning of corresponding female strips on the other member. A white dashed line has been drawn around some of these Velcro strips for ease of viewing on the prototype shown. Coupler(s) 214 allows for more easily maintaining hygiene between users without having to hand-wash the complex outer member 300.

The inner member 200 may be pre-stretched to attach to the outer member 300 via couplers 214 (e.g., Velcro attachment points), and both inner member 200 and outer member 300 may be donned at the same time by means of a zipper closure. The term "pre-stretched" here refers to the practice of placing some or all of couplers 214 (e.g., Velcro attachment points) closer together on the inner member 200 than on the outer member 300. When the two garments are attached, a tension is formed in inner member 200 such that when outer member 300 is tightened around the body part, inner member 200 returns nearer its original length, rather than wrinkling or buckling.

Inner member 200, in some embodiments, may be slightly oversized relative to outer member 300 in terms of one or both of width and length. Added width may allow inner member 200 to act as a zipper guard (a textile barrier behind the zipper teeth) to protect the wearer from the teeth of the zipper of outer member 300. Added length may protect portions of the wearer's body, such as the lower portion of the wearer's calf and shank, from irritations that might be caused by moving elements during actuation of exosuit 10. In particular, referring ahead to FIG. 11, FIGS. 12A, 12B, 12C, and FIGS. 13A, 13B and 13C, inner member 200 may protect the wearer's calf (or other relevant body part(s)), from other components of exosuit 10, such as actuation cables and load cell sensors that may be routed in proximity to the body part.

In order to improve anchoring and comfort, in some embodiments, anti-slip material 212 may be added to the inner surface of the inner member 200. Consider that the frictional force holding the flexible anchor element in place can be described by $F_F=F_N*\mu$. By using materials with a higher coefficient of friction against the underlying tissue, the resultant frictional force increases proportionally, resulting in an anchor element which can resist higher loads. Alternatively, given a required $F_F$ needed to resist a given load, the required normal force $F_N$ may be reduced if the coefficient of friction is increased. This reduced force can be greatly beneficial for the comfort and safety of the wearer. Anti-slip material 212, in various embodiments, may be any material having a coefficient of friction suitable for providing frictional engagement with the skin of the wearer (or possibly with clothing, such as a base layer, if worn underneath inner member 200). In the representative embodiment shown, anti-slip textile 212 is made of fabrifoam, a polyurethane coated fabric, but it should be recognized that any other material suitable for frictionally engaging the skin of the wearer (or a base layer textile worn by the wearer), such as polyurethane-polyester blends, silicone, adhesive (could be a disposable/removable adhesive layer). In some embodiments, anti-slip material 212 may have more elasticity than body layer 210—in such cases, vertical stitching lines spaced evenly around inner member 200 provide a suitable construction for coupling body section 210 and anti-slip material 212 in a manner that prevents the anti-slip layer 212 from stretching in the vertical direction, while still allowing stretch across the width of the inner member 200. In other embodiments, the anti-slip material 212 may be fused directly to body material 210, for example, via lamination or curing, to ensure that frictional forces applied to anti-slip material 212 are appropriately transferred to the body material 210, and by extension the outer member 300.

Anti-slip material 212 may be present in strategic areas to increase friction with the wearer and reduce slipping. For example, anti-slip material 212 may be situated at key stress points where the external forces acting on outer member 300 cause localized areas of slipping or deformation. Further, inner member 200 may be designed such that anti-slip material 212 is less likely to engage the wearer's skin during the donning process, thereby making it easier to put on and take off. For example, positioning of anti-slip material 212 along the top edge of inner member 200, as shown in FIG. 3, may allow for inner member 200 and outer member 300 to be easily repositioned on or rotated about the body part prior to zipping up outer member 300. Once outer member 300 is fully zipped (or otherwise pre-tensioned to a similar degree), the anti-slip surface 212 of inner member 200 comes into contact with the wearer, and outer member 300 is frictionally secured in place around the body part. At this point, it may be difficult to reposition inner member 200 and/or outer member 300 on the body part. In prototype testing, configurations of anchor member 100 having anti-slip material 212 on less than the entire inner surface of inner member 200 were found to be more easily repositioned during the donning process as compared to those configurations having anti-slip material 212 on the entire inner surface, thereby making the donning process less onerous and time consuming.

Additionally or alternatively, anti-slip material 212 may be arranged in strategic patterns for similar purposes. In some embodiments, anti-slip material 212 may be patterned or perforated such that spaces or gaps exist along portions of inner member 200 through which sweat and heat can be wicked away from the body part and through body section 210 of inner member 200.

Embodiments of inner member 200 may be manufactured with various thicknesses to accommodate body parts of various sizes. For example, if a user is slightly too large for an outer member 300 in size small, but the medium outer member would be too big, we can adjust for the difference by using a thicker or denser inner member layer. Since the inner members are typically much simpler and cheaper to fabricate than outer member 300, this allows us to have fewer sizes of outer member 300, and more sizes of inner member 200.

Inner member 200 may also be fabricated with variations in elastic modulus and/or thicknesses throughout its profile. A challenge especially present when referring to a patient population relates to their not necessarily having the optimal muscle geometry to achieve proper anchoring. For example, it is common among stroke survivors to have weakened or atrophied calf muscles, which results in the calf muscle tapering off in a substantially conical fashion down from the knee. Typical calf structures have a muscle belly at some point below the knee which is at least slightly larger in circumference than the measurement around the tibial tuberosity (typical narrowest point just below the knee).

To better be able to address populations without optimal muscle geometries, a thickness of inner member 200 may vary along at least a portion of inner member 200 to better interface with the geometry of the underlying musculature. The varying thicknesses throughout the profile of the inner member 200 may be tailored such that the inner surface of inner member 200 may conformably engage the geometry of the underlying musculature, while the outer geometry of the inner member is presented with a more generalized shape. Outer member 300, which secures to the outside of inner member 200, may in turn be fabricated with a complementary, general shape and thereby securely attach to inner member 200. With inner member 200 securely engaging the body part, and outer member 300 securely engaging inner member 200, the overall anchor member 100 securely engages the body part.

Inner member 200 may also be designed with thickness variations configured to complement a geometry of the underlying body part for promoting a secure anchor interface. For example, on a typical calf muscle, the wider circumference of the muscle belly compared to the region just below the knee creates an opportunity for the anchor member to mechanically lock around the top of the calf. When presented with an atrophied calf, or other presentation which does not provide this geometry, the inner member could be designed to increase in thickness at the location where we would expect to see a muscle belly, and thus provide an optimal geometry to interface with outer member 300.

An exciting opportunity with developing these custom inner members 200 is that it should be feasible to maintain a standard interface to the outer member 300 of the exosuit. This would allow the potential for developing custom fit inner member 200 solutions on an individual basis while still maintaining a standard set of sizes for the more complex elements of the exosuit. Each wearer would potentially have their own unique inner member 200 with mechanical and geometric properties for optimal anchoring, fit, and comfort, which interfaces with a standard size outer member 300. This interface could be as simple as Velcro closures, but could also use a number of other attachment mechanisms (zippers, hooks, magnets, snaps). Similarly, an individual wearer could purchase just one outer member 300, and have newly customized inner members 200 made as his/her underlying musculature changes, perhaps in response to athletic training, physical therapy sessions, or continued deterioration due to disease or aging.

Varying the thickness or elastic modulus of the inner member 200 would also produce other benefits beyond improving the underlying geometry. A thicker or more dense layer behind the Boa laces of outer member 300 could help better distribute the pressure points caused where the laces cross. Increasing the thickness or density in areas that can tolerate higher pressures, such as the belly of the calf muscle, or the patellar tendon, could provide directed pre-compression in a more comfortable way. Alternatively, varying the thickness or elastic modulus to create a "donut" or indent around critical areas such as the peroneal nerve or major blood vessels could offload pressure from these areas to help prevent discomfort or even nerve crush injuries.

One of ordinary skill in the art will recognize, in view of the present disclosure, that the principles described herein may be adapted to anchor members for other body parts without significant modification, if any, to accommodate various geometries and underlying tissue and musculature. For example, when anchoring to the upper arm, the thickness profile of inner member 200 may be adapted to offload pressure from brachial nerves and arteries. Inner member 200 may also be designed such that it may flip back over the distal end of an arm or thigh outer member 300 (i.e. fold back up onto the outer surface of outer member 300) to cushion the distal edge of the outer member 300. This may prevent or mitigate any discomfort that may occur should movement of the elbow or knee cause a pinch point against the bottom of the anchor member. At the waist, inner member 200 and outer member 300 could potentially take on more of an hourglass shape to target the compressive forces at the iliac crest, while accommodating movement at the hips or the presence of subcutaneous fat at the belly.

In some embodiments, inner member 200 may be fabricated with varying thickness, density, or elastic modulus in its profile. Additionally or alternatively, inner member 200 may be provided with pockets 220 or attachment points for receiving pre-formed inserts 230 for imparting a desired thickness, density, or elastic modulus in a particular area, as shown in FIG. 4 and FIG. 5. These preformed inserts could either be fully contained within the pocket of the inner member, or else they could attach to the surface of the body via an adhesive or high friction layer. Different sized inserts could be used to accommodate varying severity of atrophy in the underlying muscles. Further, inner member 200 may be provided with reservoirs configured to be inflated or deflated with air or other suitable fluid for providing a desired fit and profile.

In some embodiments, this entails creating pockets or attachment points in inner member 200, so that pre-formed inserts can be added to increase the bulk of the underlying body part in optimal locations. Another concept entails having increased thickness of the inner member over portions of the calf where we desire larger geometries, for example across the belly of the calf muscle.

For the specific iteration of the calf, one proposed pressure redistribution method could be as follows: increase inner member thickness and/or density at the belly of the calf muscle, as this region is capable of tolerating higher pressures, and reduce the inner member thickness/density where the peroneal nerve lies just behind the fibular head. To further offload pressure from this location, increase the inner member thickness/density in the area just adjacent to the fibular head to create a "donut" around the sensitive area. Since the outer member 300 applies a circumferentially uniform pressure, these differences in thickness will result in higher or lower areas of pressure from the pre-compression levels. Similar methods could be used to help redirect the compressive forces created during dynamic compression of substantially inextensible textile element 340 as well, as later described.

Similar methods could be used on an individual basis to direct pressures to more tolerant regions and offload pressure from previous scars, blood vessels, or other sensitive locations.

Figure 6:
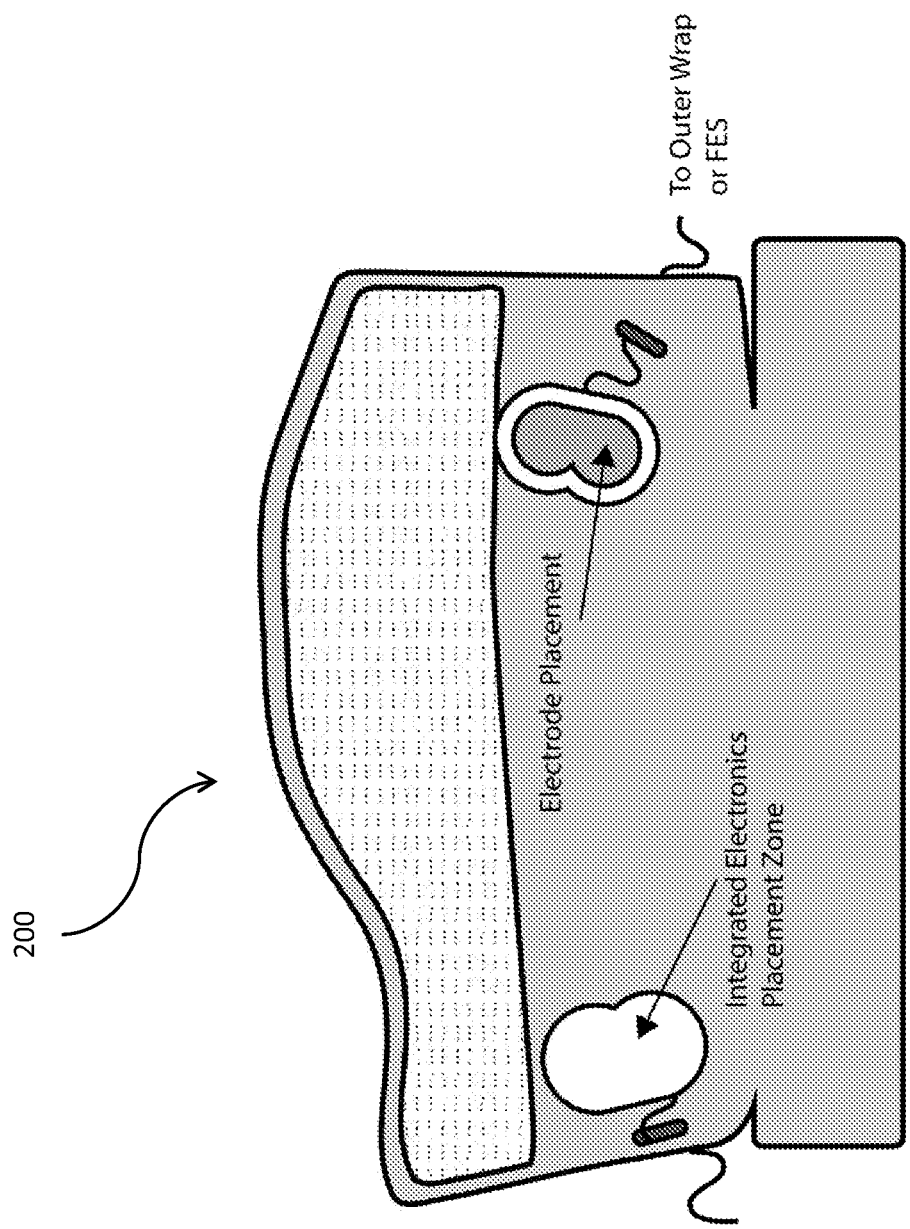
FIG. 6 shows an inner member having integrated electronics and electrodes, in accordance with an embodiment of the present disclosure.

FIG. 6 shows an inner member 200 and an outer member 300 having integrated wiring, electrodes or electronics. For example inner member 200 could have electrodes placed at key locations to as to either sense muscle activity or apply electrical stimulation to muscles for functional electrical stimulation (FES). The electrodes could be connected to wiring that could interface directly to an FES or robotic system (wired or wireless) or could have a physical connector that interfaces to the outer member that may be connected to controllers for an exosuit, wearable robot or FES system. Electrodes, conductive surfaces, wiring or sensors could be added to the liner 200 and wrap 300 during the component manufacturing process or added discretely after their production. The location of these electrodes could be at discrete locations or distributed evenly throughout the liner 200. The liner 200 that has electrodes integrated into could enable the electrodes to be placed repeatably over certain parts of the anatomy to ensure they sense or stimulate in the same location every time it is used.

Additionally, inner member 200 or outer member 300 may have other sensors, electronics or actuators directly integrated into it. For example, inner member 200 could have pressure or force sensors incorporated into it for monitoring or controlling the interaction pressures/forces with the wearer. These sensors could monitor pressure and/or force normal to the body and skin, or in some other direction such as shear. In other embodiments, the sensors could monitor the temperature, perspiration or other physiological measures of the wearer. An example means to monitor this would be using galvanic skin response. In yet other embodiments the sensors could consist of optical or acoustic sensors that could be embedded in inner member 200 or outer member 300 to noninvasively measure changes in underlying tissue characteristics or blood flow either outside or inside the body. Additional types of sensors could be inertial measurement units (IMUs), accelerometers or gyroscopes.

Inner member 200 or outer member 300 may also have embedded sensors that can detect movement, migration or slippage of the components relative to the user, or of outer member 300 relative to inner member 200. For example, a magnetic component could be embedded in inner member 200 and a hall effect sensor placed in outer member 300. Upon initially donning, an initial signal value could be recorded and this value could be monitored over time to measure relative movement of outer member 300 relative to inner member 200. To monitor movement of inner member 200 or outer member 300 relative to the wearer, optical or acoustic sensors could be integrated to monitor movement relative to anatomic landmarks inside or outside the body. Alternatively, if the baseline pre-compression value or distribution changes over many walking cycles, this could be used to monitor movement of inner member 200 and outer member 300, or alert the user that they may need to be adjusted. Alternatively a flexible strain sensor as part of inner member 200 or outer member 300 (e.g., of a calf anchor member) could be attached to a distal body anchor (e.g. a foot anchor member) and changes in the value of this sensor could indicate movement of the inner member 200 and outer member 300 relative to the skin.

Outer member 300 may also have force sensors and associated wiring and electronics integrated into it where the actuation cable attaches to apply the force. An example of this could be a compliant, textile sensor that forms a strap that can record a force reading, for example, to measure the tensile force being applied by an external actuator.

Embodiments of flexible anchor member 100 having integrated sensors and wiring could enable inner member 200 to be easily put on as described, but then have sensing or stimulation happen through outer member 300 via a connection to inner member 200. Having connectors or sensors in both inner member 200 and outer member 300 could enable repeatable placement of these components relative to each other. Additionally, outer member 300 may have other sensors, electronics, actuators directly integrated into it. An example would be analog or digital electronics (e.g. a microprocessor) that could perform local signal conditioning or analysis before a signal would be transmitted via a wired or wireless connection to another system component such as a user interface or control hardware that runs a system control algorithm. In the case of an array of electrodes for sensing or stimulation the signal could be multiplexed to simplify wiring and signal transfer. A similar approach could be performed with a distributed array of pressure sensors in order to obtain a measurement of the distribution of the pressure around the body (either all of it or at key locations).

Outer Member 300

Figure 7:
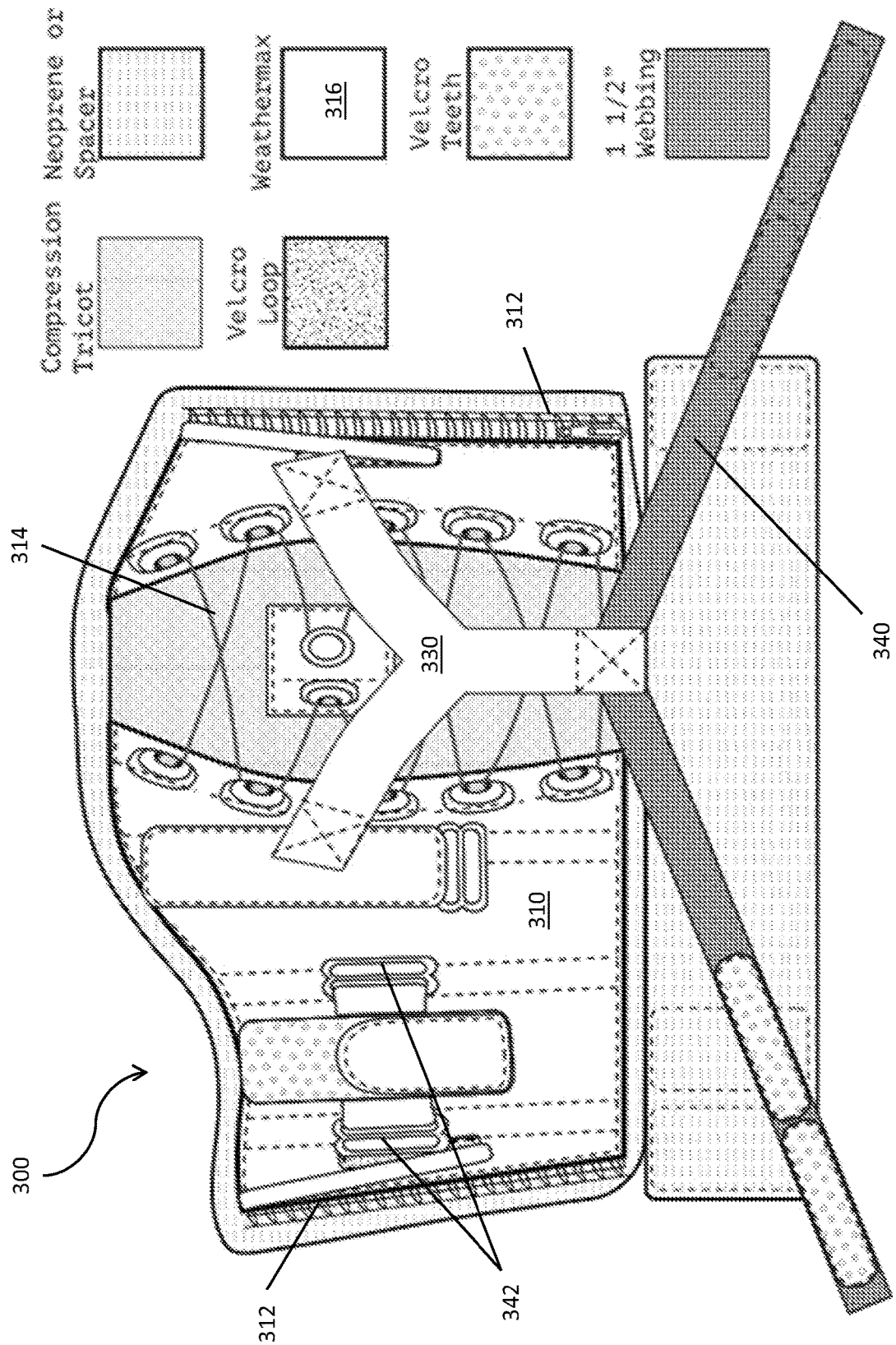
FIG. 7 shows an outer member of a flexible anchor member, in accordance with an embodiment of the present disclosure.

Referring to FIG. 7, in a representative embodiment, outer member 300 may include a body section 310, one or more stiffening elements 320, a force transfer coupler 330, and at least one substantially inextensible textile element 340.

Body section 310, in various embodiments, may be configured for positioning over inner member 200 and about the body part. In the representative embodiment, body section 310 includes a flat woven textile that wraps around the body part, where opposing edges are jointed together by any suitable fastener 312 known in the art, such as zippers, snaps, and hook and loop fasteners. Body section 310 may further include a mechanism 314, such as laces or a BOA system, for further pre-tensioning body section 310 about the body part and generating a pre-compression force thereon.

Figure 8:
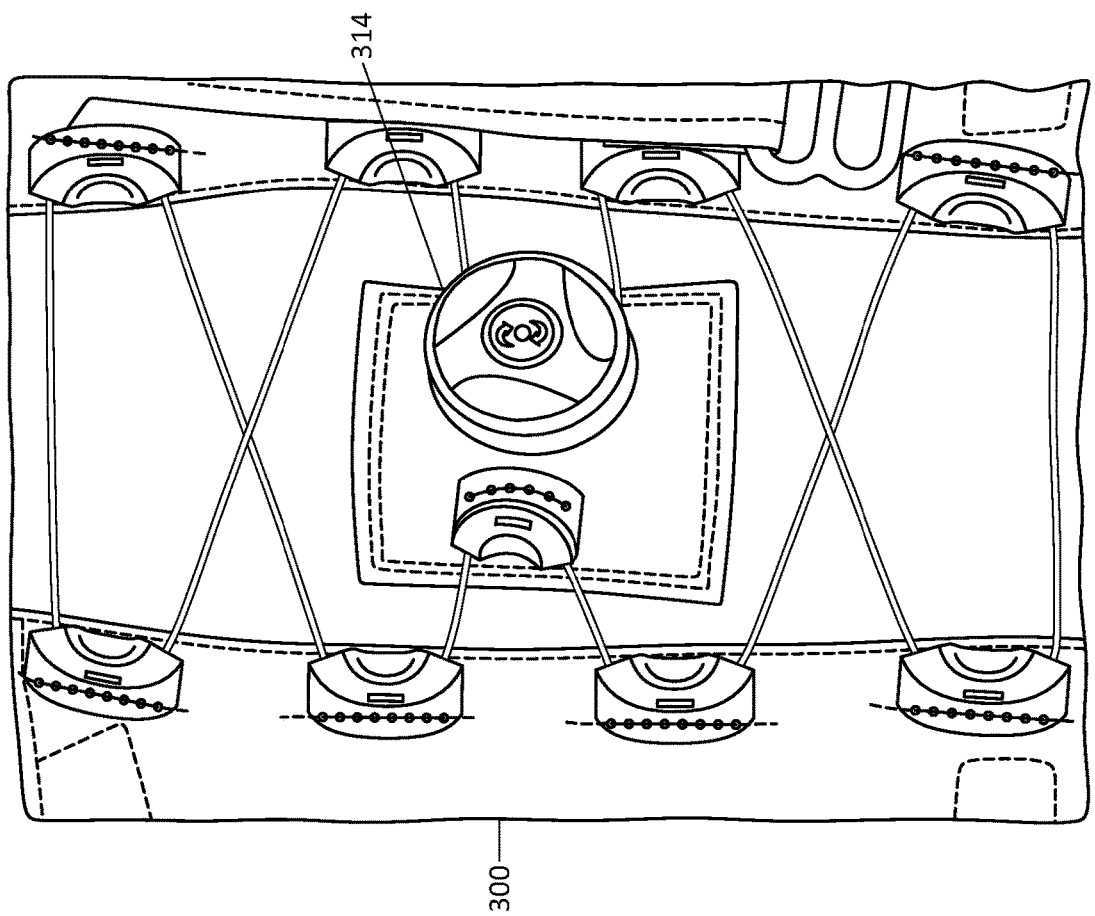
FIG. 8 shows a close up view of an embodiment of a lace structure for generating a pre-compression force about the body part, in accordance with an embodiment of the present disclosure.

FIG. 8 shows a close up view of one embodiment of the lace structure 314 which tightens across the back of outer member 300. A non-elastic "island" may be provided to allow for placement of the Boa dial in the center of the lace pattern. Optimally, the Boa dial, lace eyestay, and island platform could be combined into a single element that could be sewn to the elastic tongue.

Another embodiment of the lace structure 314 involves adding markings to the lace material. For example, we could place 10 dots each 2 mm apart on the laces. As the lace material is pulled in to the Boa dial, the markings will draw closer or further away from the dial. In this manner, we can use these markings on the laces to set the dial to a consistent value on a given wearer from one day to the next. For example, if a user does well at the pre-compression level associated with dot #3, we can consistently set the system up to provide the same level of pre-compression each time the system is used.

Of course, in other embodiments (not shown), outer member 300 could have a closed, sleeve-like shape (e.g., cylindrical, conical, or tapered at both ends) configured to be pulled onto the body part. In some embodiments, conical-shaped sleeves may be preferred, as the tapered shape may resist slippage of the sleeve in the direction of the larger end by mechanically locking with the underlying musculature and/or skeletal structure.

It should be recognized that, for embodiments in which anchor 100 in includes both outer member 300 and inner member 200, the potential for skin irritation being caused by overlapping edges in flat embodiments of outer member 300 may be of less concern than it was with inner member 200, as in various embodiments, inner member 200 may protect the skin from contact with outer member 300 in at least this region.

In various embodiments, body section 310 may be made from any textile or similar material having sufficient flexibility for accommodating flexing and other movements associated with the tissue, underlying muscles, joints, etc. of the body part, while still having sufficient shear strength and material stiffness to resist significant deformation under loads applied thereto during actuation of the exosuit. Example materials include, without limitation, sailcloth (Dimension Polyant), Weathermax 50/80 (Safety Components), Typhoon (Springfield LLC, now Milliken), Cordura (Seattle Fabrics), or laminations thereof, amongst other suitable materials or combinations thereof. In some embodiments, two or more different fabrics may be layered together (and bonded, for example, via lamination) so as to leverage beneficial properties of both materials.

Referring back to FIG. 7, outer member 300, in various embodiments, may include a substantially inextensible textile material 316 configured for directing a force applied by an actuator to act upon all or a portion of the body part. In the embodiment shown in FIG. 7, all or most of body 300, as well as of force transfer coupler 330, may be fabricated of substantially inextensible textile material 316, shown here in this embodiment as a Weathermax fabric. Typhoon or other similar suitable material may be used in other embodiments. External forces applied to force transfer coupler 330 by an actuator are transferred up arms 332a, 332b (later shown in FIG. 10) of the force transfer coupler 330 and to body section 310 of wrap 300. By wrapping circumferentially around the body part, body section 310, consisting of inextensible material 316, further distributes the forces from the actuator circumferentially around the underlying body part, and additionally or alternatively directs some of this force to the surface opposite the applied force. As configured, outer member 310 may, for example, direct some or all of an actuation force applied at the posterior of the calf to instead act on the anterior region and shin.

In other embodiments, only a portion of body section 310 is made from substantially inextensible material 316. This portion(s) of outer member 310 may extend between a first location and a second location of body section 310 so as to provide a pathway between the first and second locations along which to direct all or a portion of an applied force from the first location to the second location. For example, in an embodiment, substantially inextensible material 316 may extend between a first location associated with an input from force transfer coupler 330 and a second location associated with a portion(s) of the underlying body part on which it is desired to deliver all or a portion of the applied force. In some embodiments, the second location may be associated with a portion of the underlying body part suitable for comfortably supporting the applied load, such as a bony anatomical feature (e.g., iliac crest of the waist, heel bone of the foot, shoulder bone of the shoulder). In addition to improved comfort, directing all or a portion the applied force onto a bony anatomical feature may improve the stiffness of the wearable system due to reduced energy transmission losses that may otherwise occur on softer portions of the body due to tissue or muscle compression. Another suitable portion of the underlying body part for comfortably supporting the applied load may, in some embodiments, include areas with resilient tissue or muscle, or areas that undergo little or no muscle contraction. In most cases, it is preferable to avoid areas where blood vessels or nerves are close to the surface of the body part or otherwise would be uncomfortably compressed by the applied force.

Sweat and temperature management may be of concern when dealing with long term wear of outer member 300. For this reason, we present another embodiment of the outer member body section 310 with a breathable mesh spacer to reduce incidence of sweating. Outer member body section 310 may additionally or alternatively include other breathable materials and constructions for this purpose as well.

Figure 9:
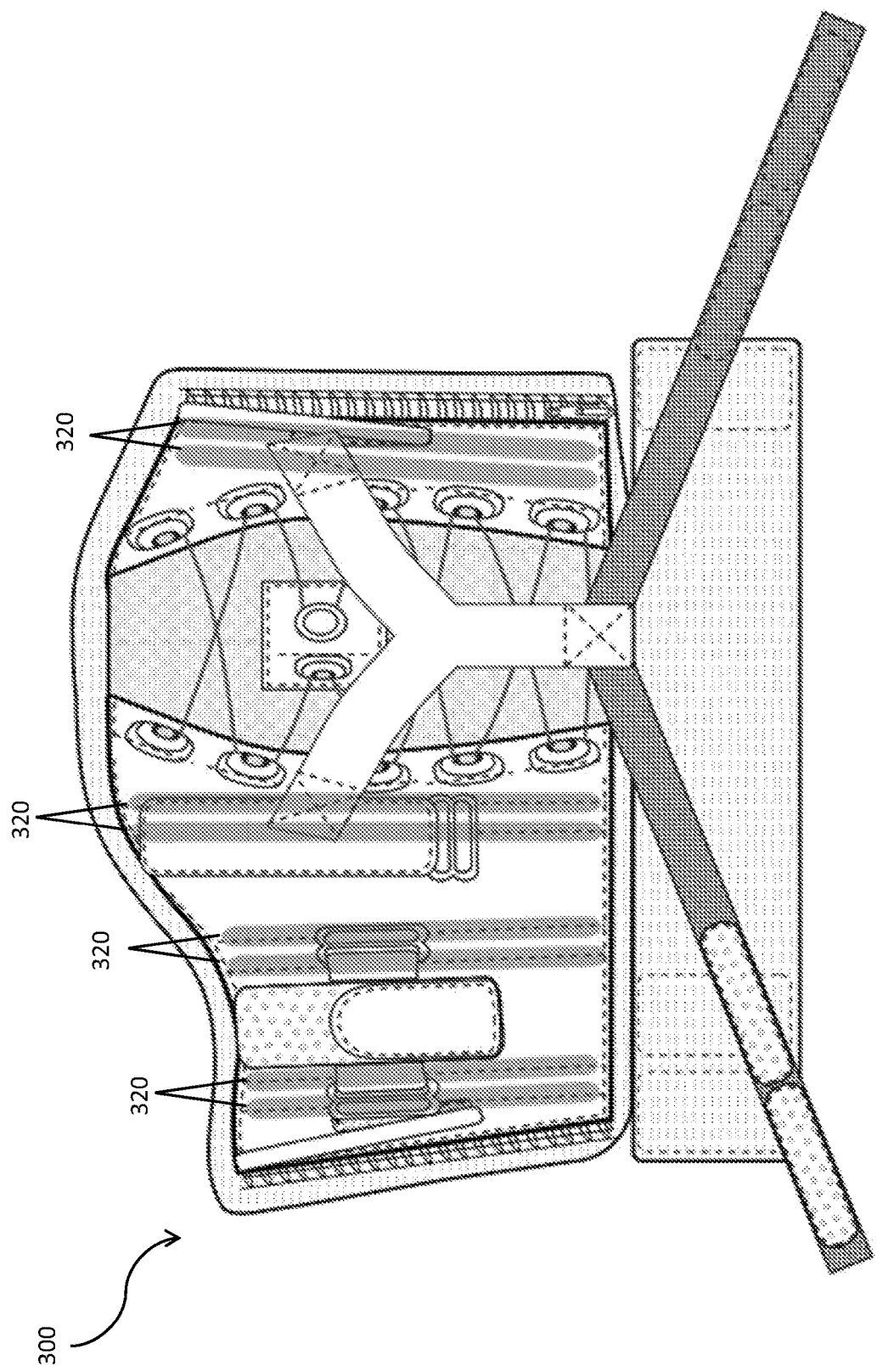
FIG. 9 shows an outer member having a plurality of stiffening elements, in accordance with an embodiment of the present disclosure.

Referring to FIG. 9, outer member 300, in various embodiments, may further include one or more stiffening elements 320 made from semi-rigid material(s), such as corset boning. Stiffening elements 320 may be included to provide additional stiffness in the longitudinal (here vertical on the calf) stiffness along the length of outer member 300. When the outer member 300 is tightened to the wearer, stiffening elements 320 render the outer member 300 substantially incompressible in the longitudinal direction, yet allow outer member 300 to remain quite flexible in the circumferential direction to accommodate different body shapes and sizes. The addition of stiffening elements 320 allows the textiles of the outer member 300 to resist buckling or wrinkling under longitudinal loads, and operate in either tension or compression.

In one aspect, this allows us to attach force transfer coupler 330 higher up on the outer member 300 (i.e., away from the bottom edge of outer member 300 and to a central portion or upper portion of outer member 300) to increase the available travel distance between force transfer coupler 330 and the cable end anchor (in this case located on the foot). The result is that with more available travel, higher forces can be generated across the targeted joint. Additionally, it may be desirable to move load bearing attachment points higher up on the outer member 300 in order to accommodate other mechanisms that can be added to the outer member 300.

With the addition of stiffening elements 320, we can also extend the outer member 300 distally beyond the point where an actuation cable may attach (here, at force transfer coupler 330, later described), and thereby achieve a greater surface area in contact with the wearer. Consider that the wearer's perception of comfort is more closely tied to the value of the pressure, P, applied to their underlying tissues, rather than the overall normal force. Given that $P=F_N/A$, we can substantially improve wearer comfort and reduce risk of injury to the wearer by distributing a given normal force over a larger surface area. Alternatively, increased surface area may result in the ability to more comfortably apply a higher normal force, which will result in greater frictional force between outer member 300 and inner member 200, and also greater frictional force between inner member 200 and the underlying body part, which helps prevent slippage of outer member 300 on the body part.

Stiffening elements 320, in some embodiments, may be positioned at the points under the most load. For example, it may be advantageous to include stiffening elements 320 around the location where the actuation member (e.g., cable) couples to outer member 300. In the present embodiment, this would be an area surrounding force transfer coupler 330. In other embodiments, stiffening elements 320 may additionally or alternatively be spaced evenly around the entire circumference if additional stability is desired. Stiffeners 320, in an embodiment, could run the entire longitudinal direction of outer member 300. In another embodiment, stiffeners 320 could a portion of the length of outer member 300, which may improve comfort and allow for the presence of other outer member elements (e.g., elastic panels). Stiffeners 320 could also be shaped or placed at varying angles to direct forces along desired pathways through outer member 300, for example, around an elastic element to a more stable woven element.

Figure 10:
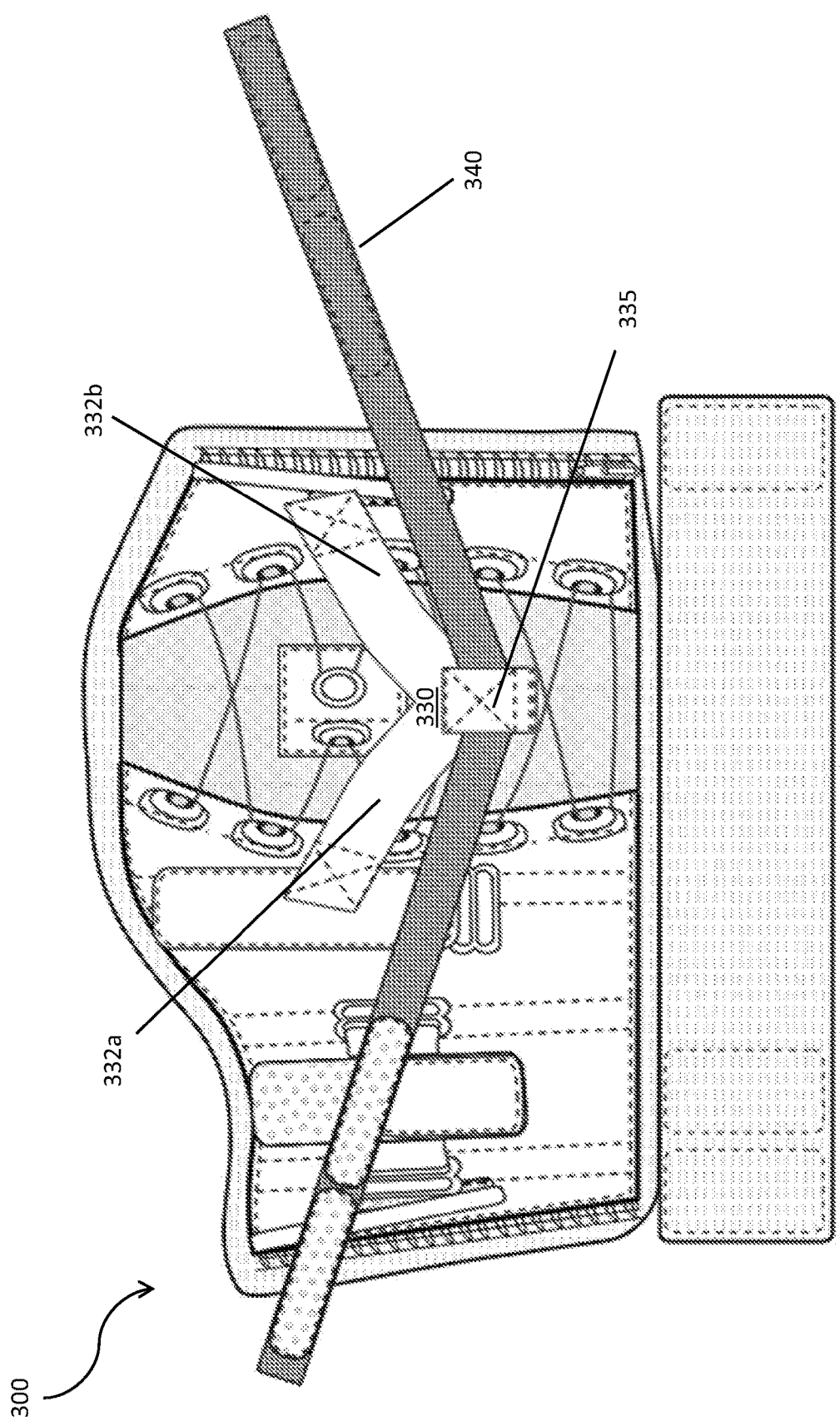
FIG. 10 shows a force transfer coupler for coupling an actuator to an substantially inextensible textile element and an outer member of a flexible anchor member, in accordance with an embodiment of the present disclosure.

Referring to FIG. 10, outer member 300, in various embodiments, may further include a force transfer coupler 330 for coupling a source of an applied force (e.g., an actuator cable) to outer member 300. Force transfer coupler 330, in the particular embodiment shown, may be Y-shaped with arms 332a, 332b and stem 334. As shown, arms 332a, 332b may stretch upwards and outwards, with their distal ends fixedly connecting to a rear portion of outer member body section 310. Stem 334 may freely extend downwards from the junction of the proximal ends of arms 332a, 332b, with its distal end remaining unconnected to outer member body section 310.

In the embodiment shown, an intermediate portion of substantially inextensible textile element 340 may be fixedly coupled (e.g., sewn) with stem 334, as shown. If substantially inextensible textile element 340 is viewed as two substantially inextensible textile elements, then it should be understood that in the embodiment shown, the proximal ends of the two substantially inextensible textile elements may be fixedly coupled with stem 334. It should be appreciated that in other embodiments, rather than being separate from body section 310, substantially inextensible textile element 340 may instead be integrated into body section 310 of outer member 300. In such an embodiment, it may not be necessary to manually wrap substantially inextensible element 340 around the outside of body section 310, but rather substantially inextensible element 340 may be situated within body section 310 and allowed to translate freely therewith.

The distal end of stem 334 may be folded upwards to form a saddle 335 for attaching a cable connector 336 (shown in later figures) to outer member 300. Cable connector 336 may serve as an attachment point to outer member 300 for an actuation member (e.g., cable) of the exosuit 10.

Cable connector 336, in the embodiment shown, is free to slide up and down within saddle 335, and thereby acts as a pulley that self-adjusts to the point where the loads applied by the cable are evenly distributed between the combination of arms 332a, 332b and substantially inextensible textile element 340. In particular, when a downward load due to actuation is applied to the cable connector 336, 50% of this load is distributed to arms 332a and 332b of force transfer coupler 330, and 50% of the load is distributed to the substantially inextensible textile element 340. Should either the outer member 300 slip, or the substantially inextensible textile element 340 constrict about the body part (and therefore lengthen), the cable connector 336 can slide along the saddle 335 to find a new equilibrium such that this distribution of forces is maintained.

Substantially inextensible textile element 340 may extend from saddle 335 on the rear of outer member 300, and wrap circumferentially around the body part (e.g., the wearer's calf in the representative embodiment). Depending on the embodiment, substantially inextensible textile element 340 may wrap partially or fully about the circumference of outer member 300. As configured, when an actuation load is applied to force transfer coupler 330, the saddle 335 pulls on substantially inextensible textile element 340, causing substantially inextensible textile element 340 to translate in the direction of the applied force, and thereby temporarily constrict about body section 310 of outer member 300 and the underlying body part, similar to the tightening of a shoe by pulling on the ends of the laces. This temporary increase in normal force applied by the flexible anchor element 340 results from the tightening of substantially inextensible textile element 340 in response to applied actuation loads. This is referred to herein as dynamic compression.

By configuring outer member 300 to generate dynamic compression, the amount of pre-tension required to hold outer member 300 securely in place on the body part during operation of the exosuit is reduced. For an explanation, please refer to the free body diagrams in FIGS. 15A, 15B, and 15C. Consider that the magnitude of the frictional force preventing the flexible anchor member from slipping is a product of the normal force and the coefficient of friction, as shown in equation (1):

$$F_F = \mu * F_N \tag{1}$$

where $F_F$=Force of friction, $\mu$=coefficient of friction between flexible anchor member and underlying tissue, and $F_N$=Normal force applied to anchor element.

Under unloaded conditions (FIG. 15A), the calf outer member must be pre-compressed to a degree such that the force of friction can overcome the force of gravity (in this case, gravity acts perpendicular to the normal force) as shown in equations (2) and (3):

$$F_{F(no\ load)} = F_G \tag{2}$$

$$F_{N(no\ load)} = F_G/\mu \tag{3}$$

where $F_G$=Force due to gravity, equal to the weight of the calf outer member.

Under loaded conditions (FIG. 15B), the calf outer member must be pre-compressed to a degree such that the force of friction can overcome the force of gravity+the force of the applied load (again, with the assumption that the load and gravity are both acting perpendicular to the normal force) as shown in equations (4) and (5):

$$F_{F(load)} = F_G + F_L \tag{4}$$

$$F_{N(load)} = (F_G + F_L)/\mu \tag{5}$$

where $F_L$=Force of the applied load.

This means that the pre-compression normal forces must be increased over scenario A by a value of $F_L/\mu$ in order to resist the applied load during actuation.

Figure 15C:
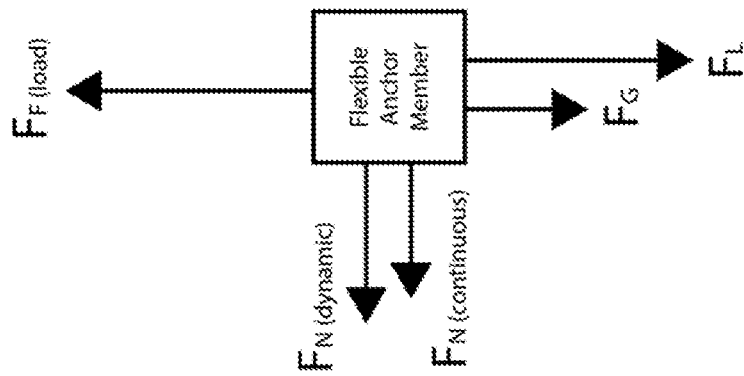
FIG. 15A, FIG. 15B, and FIG. 15C show representative free-body diagrams illustrating various forces acting on a flexible anchor member, in accordance with embodiments of the present disclosure.
Figure 15B:
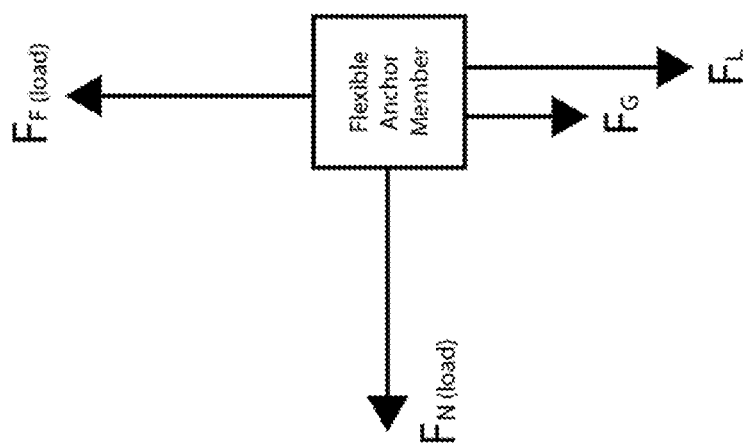
Figure 15A:
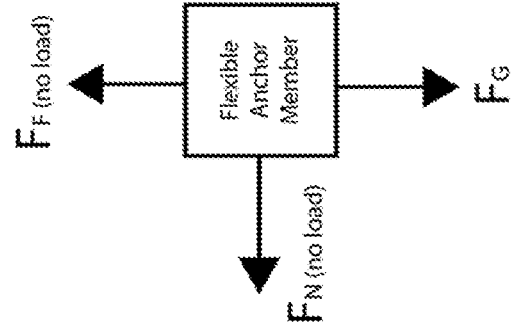

Now consider the case of a flexible anchor member with substantially inextensible textile element 340 (FIG. 15C). In response to an applied load, substantially inextensible textile element 340 may constrict around outer member 300, resulting in a temporary increase in normal force beneath the straps as shown in equations (6), (7), and (8):

$$F_N = F_{N(continuous)} + F_{N(dynamic)} \tag{6}$$

$$F_N = (F_G + F_L)/\mu \tag{7}$$

$$F_{N(Continuous)} = [(F_G + F_L)/\mu] - F_{N(dynamic)} \tag{8}$$

where $F_N$=the combined normal force during actuation, $F_{N(dynamic)}$=the temporary normal force generated via dynamic compression, and $F_{N(continuous)}$=the continuous force applied during pre-compression.

Comparing this scenario to that of scenario B, the continuous normal forces applied by the anchor member are reduced by the value of $F_{N(dynamic)}$. In the extreme case where $F_{N(dynamic)} = F_L/\mu$, the $F_{N(continuous)}$ value could be reduced to that of the scenario shown in FIG. 15A, such that the continuous normal forces are equal to that of the original no-load condition.

In some embodiments, dynamic compression may account for the entire amount of additional normal force to securely hold outer member 300 in place during actuation, thereby allowing outer member 300 to be pretensioned only to that level $F_{N\ (no\ load)}$ necessary to hold it in place during periods of non-actuation. However, in various embodiments, various losses may reduce the efficiency by which dynamic compression may be generated, and thus outer member 300 may need to be pretensioned somewhere between $F_{N\ (no\ load)}$ and $F_{N\ (load)}$. Notably, this is still advantageous from a comfort standpoint compared with having to pretension at level Y. Depending on the length of substantially inextensible textile element 340, the type of tissue beneath outer member 300, and the actuation loads applied, sometimes the applied force may cause substantially inextensible textile element 340 to effectively lengthen so much so that either saddle 335 does not function properly because cable connector 336 has no room to slide, or the substantially inextensible textile element 340 drop so low that cable travel is reduced to the point that the desired force cannot be achieved given stiffness of the system and the available travel. It is important to note, for clarity, that the lengthening of straps 340 is not necessarily due to a stretching of the straps 340 themselves (they may be inelastic), but rather results from the translation of substantially inextensible textile element 340 as it constricts, which reduces the circumference of the straps 340, causing straps 340 to get effectively longer.

FIG. 11, FIGS. 12A, 12B, 12C, and FIGS. 13A, 13B, 13C depict representative configurations of force transfer coupler 330, cable connector 336, and substantially inextensible textile element 340 on outer member 300.

Figure 11:
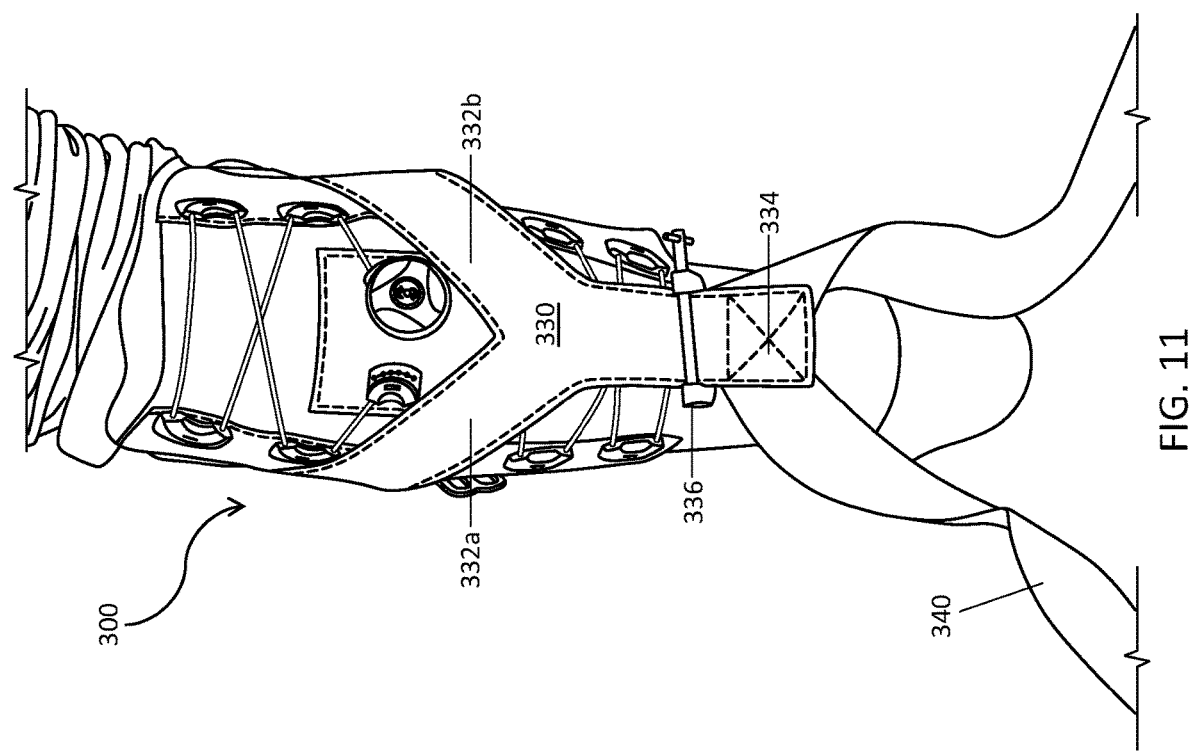
FIG. 11 shows a flexible anchor member as worn prior to circumscribing an outer member with an substantially inextensible textile element, in accordance with an embodiment of the present disclosure.

Referring to FIG. 11, outer member 300 is shown with body section 310 secured to the wearer's calf, but with substantially inextensible textile element 340 not yet wound thereabout. Cable connector 336 is slidably coupled with stem 334, and substantially inextensible textile element 340 has been sewn onto the distal end of stem 334, as shown.

Figure 12C:
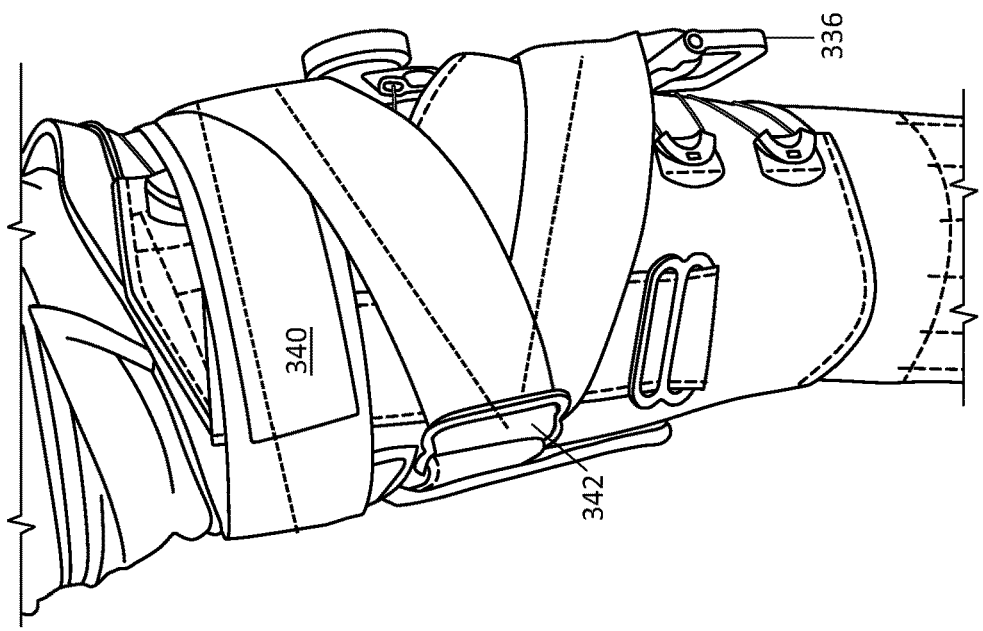
FIG. 12A, FIG. 12B, and FIG. 12C show a pathway defined by an substantially inextensible textile element fastened to an outer member of a flexible anchor member, in accordance with an embodiment of the present disclosure.
Figure 12B:
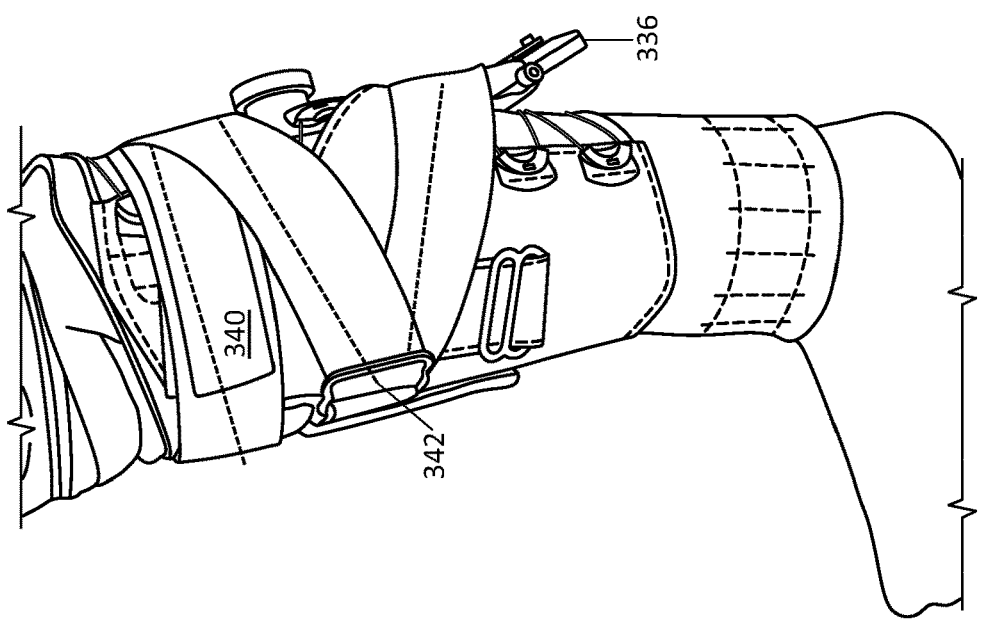
Figure 12A:
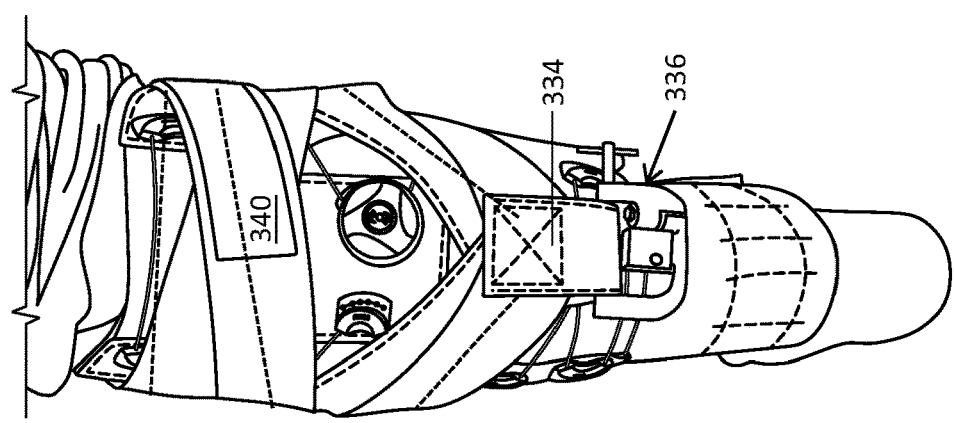

Referring to FIG. 12A, FIG. 12B, and FIG. 12C, stem 334 has been folded up to form saddle 335 and substantially inextensible textile element 340 have been wrapped circumferentially about outer member body section 310. White dashed lines have been laid over the path taken by the substantially inextensible textile element 340 to aid the reader, given the lack of visual contrast between substantially inextensible textile element 340 and outer member body section 310 in the photos.

In the particular configuration of FIG. 12A, FIG. 12B, and FIG. 12C, substantially inextensible textile element 340 have been further threaded through buckles 342 on the front of outer member body section 310. As configured, buckles 342 frictionally engage substantially inextensible textile element 340 when they are pulled in response to an applied actuator load. The friction reduces the travel of the substantially inextensible textile element 340 as they attempt to tighten about outer member 300, and thereby causes a greater amount of the actuation force to instead be diverted directly to the outer member body section 310 at buckles 342. In this way, outer member 300 may be configure reduce the amount of dynamic compression available. This may be required or advantageous in situations where the load on the substantially inextensible textile element 340 causes them to tighten so much that the effective lengthening of these straps 340 interferes with either the function of the saddle or interferes with the required amount of cable travel required for a given use, as previously described. Additionally, some wearers seem to prefer a higher, more continuous level of compression, whereas others prefer more intermittent levels of compression, and this technique allows us to accommodate both preferences. Of course, any other mechanism suitable for frictionally engaging substantially inextensible textile element 340 may be used in lieu of buckles 342.

Figure 13C:
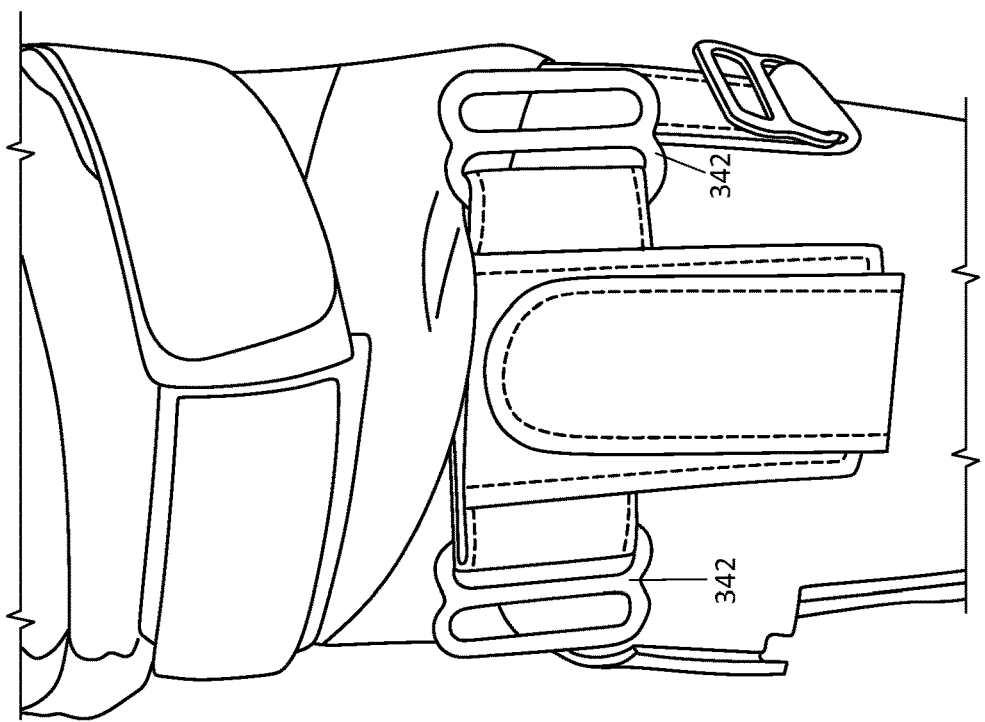
FIG. 13A, FIG. 13B, and FIG. 13C show a pathway defined by an substantially inextensible textile element freely circumscribing an outer member of a flexible anchor member, in accordance with an embodiment of the present disclosure.
Figure 13B:
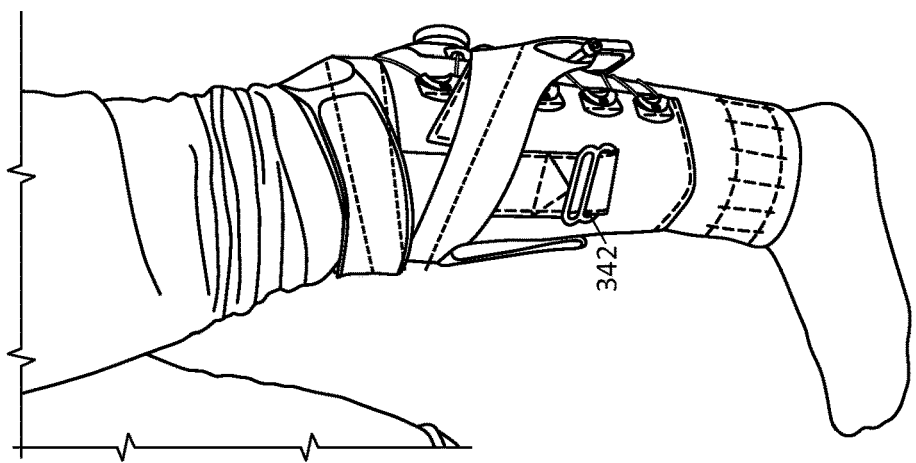
Figure 13A:
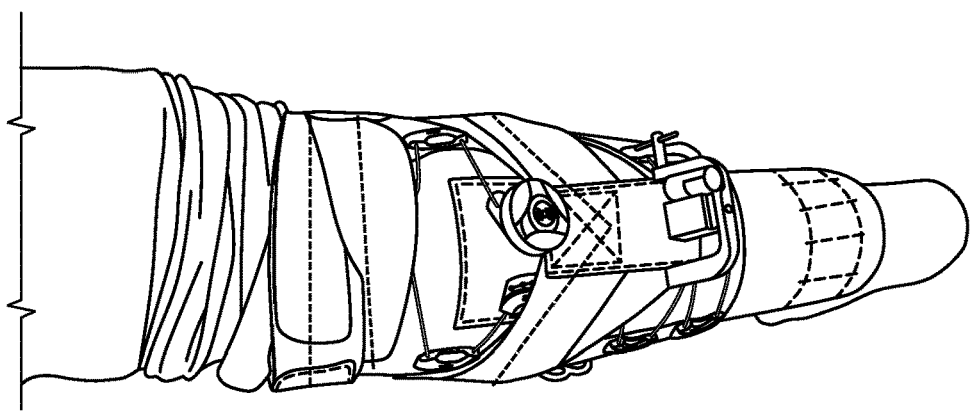

Referring to FIG. 13A, FIG. 13B, and FIG. 13C, outer member 300 is similarly configured; however, in this embodiment, substantially inextensible textile element 340 has bypassed buckles 342 and instead freely wraps around outer member 300. As configured, substantially inextensible textile element 340 may translate unimpeded about outer member body section 310, and thus the ratio of actuation forces distributed between outer member body 310 and substantially inextensible textile element 340 remains substantially equal, thereby providing for a greater amount of dynamic compression than that provided via the configuration of FIG. 12A, FIG. 12B, and FIG. 12C. As previously explained, this may advantageously improve the comfort of the wearer by reducing the amount of baseline level of pre-compression required.

Donning of Flexible Anchor Member 100

Figure 14B:
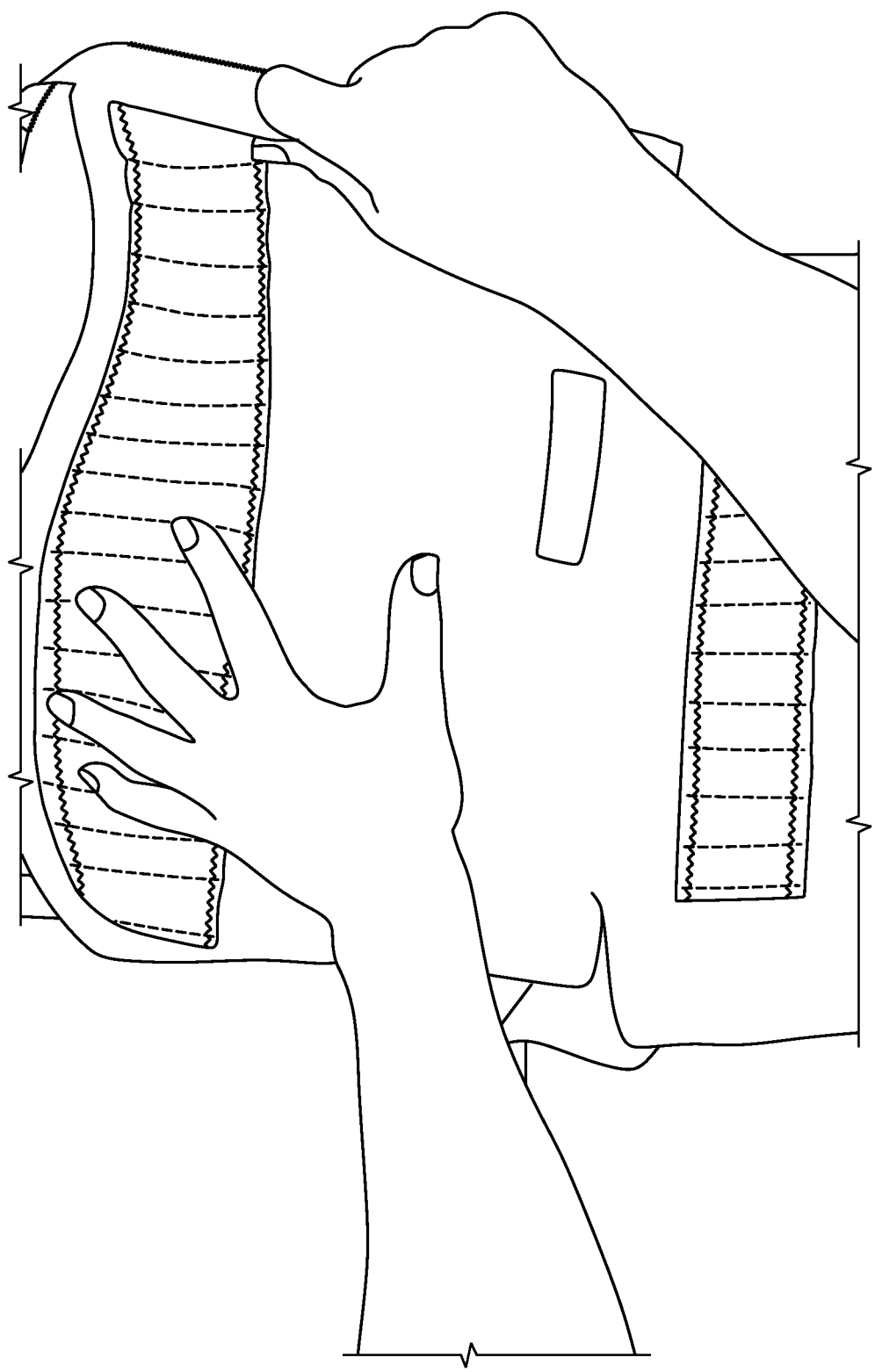

The following is a description of a process for donning an embodiment of embodiments of flexible anchor member 100 that include both inner member 200 and outer member 300, as shown in FIG. 14A. In the current embodiment, the device is donned by attaching the flat inner member to the inner surface of the outer member 300. The inner member is slightly pre-stretched in this process so that it extends beyond the horizontal edges of the outer member, as shown in FIG. 14B. This allows the inner member to perform as a zipper guard, and the pre-stretching helps to prevent wrinkling of the inner member when the outer member is compressed.

Figure 14D:
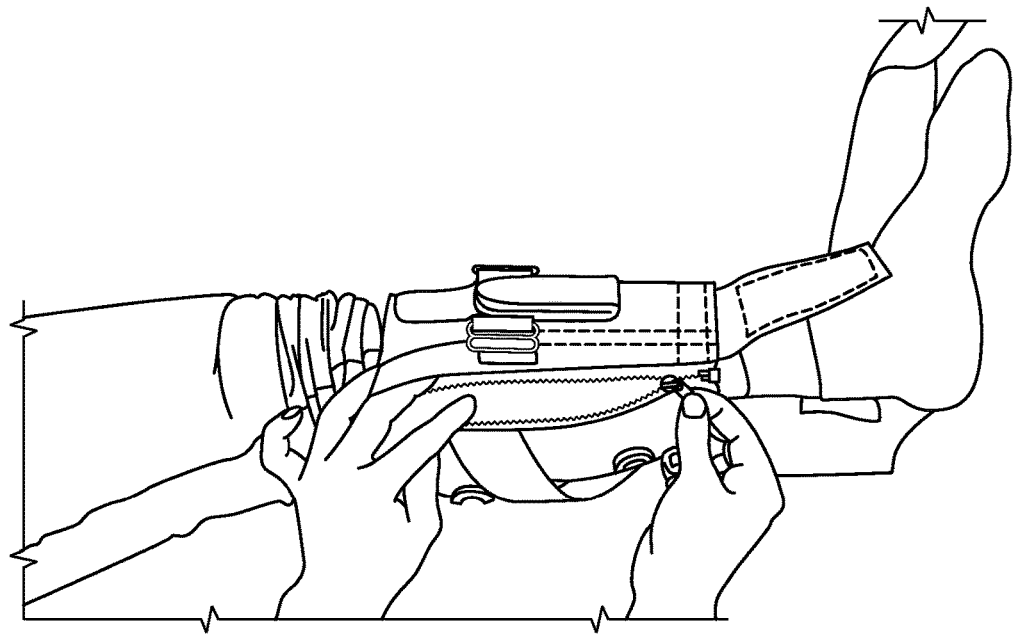
Figure 14C:
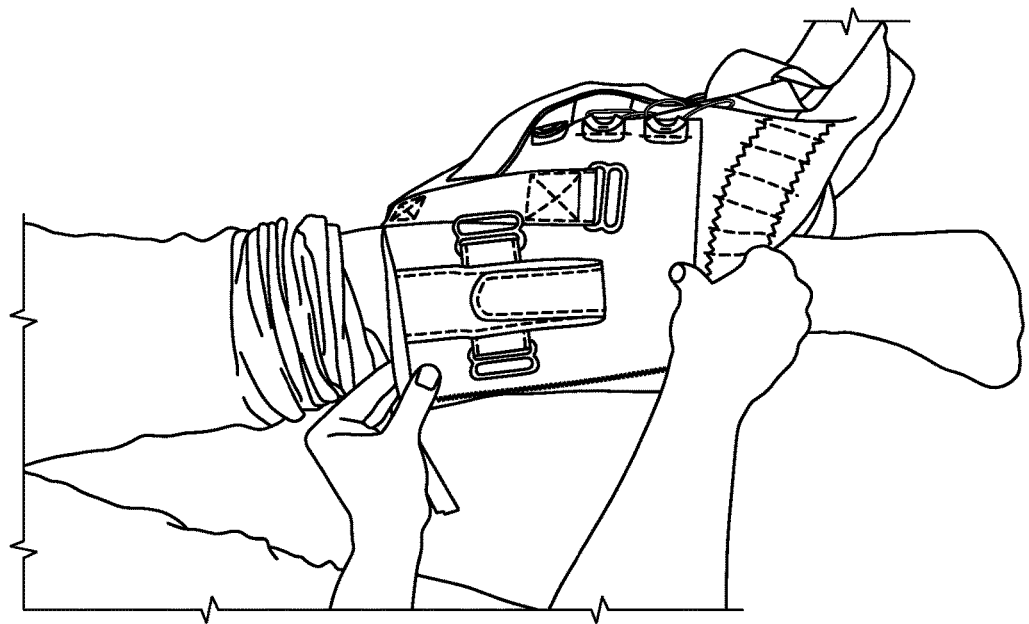
Figure 14E:
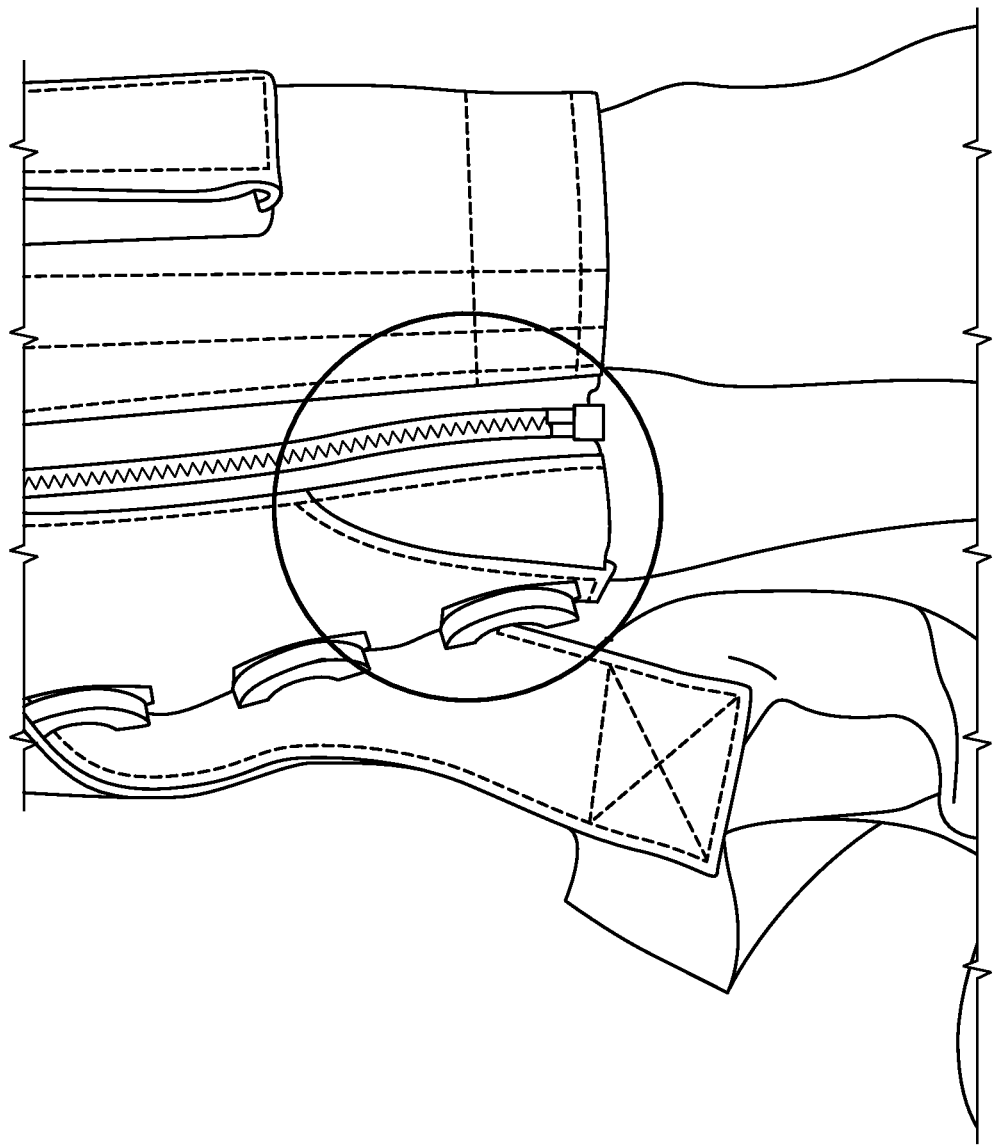

Referring to FIG. 14C, the combination outer member 300/inner member 200 is then placed either directly on the wearer's skin, or over clothing, and aligned such that the front tab (the attachment point for a dorsiflexion cable of the exosuit) is aligned with the wearer's tibia. The outer member 300 is zipped up along the medial border as shown in FIG. 14D. A small elastic tab at the bottom of the zipper, shown with a triangular shape in FIG. 14E, helps to fasten the zipper more easily. Once zipped, the boa dial on the back of the calf is turned, which reels in the laces and applies compression through the outer member as shown in FIG. 14F. This determines the pre-compression level.

Figure 14G:
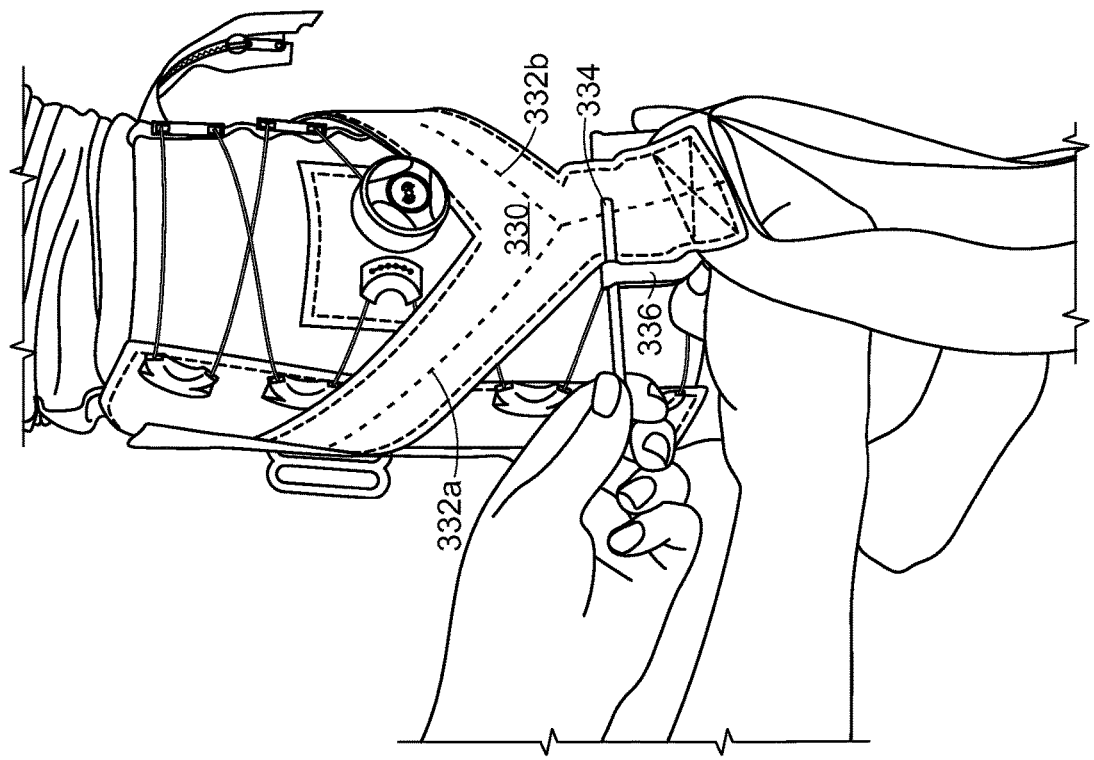
Figure 14F:
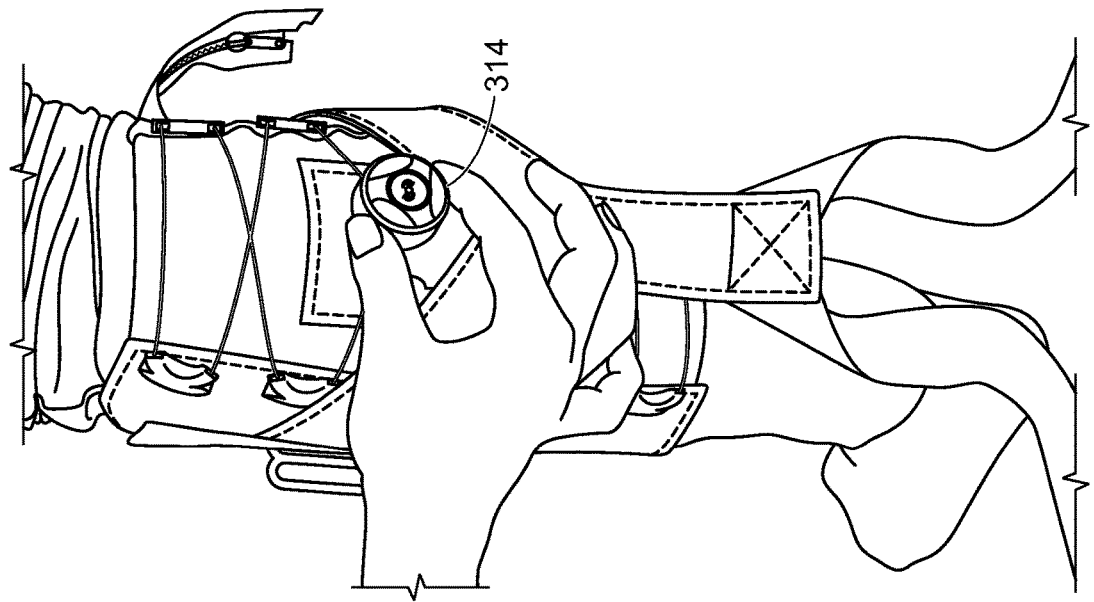

Referring to FIG. 14G, once the pre-compression has been set, cable connector 336 may be attached to stem 334 of load transfer couple 330. In the embodiment shown, cable connector 336 is essentially a metallic D-ring with a removable shank for positioning the cable connector 336 on stem 334. Of course, cable connector 336 need not be detachable, but rather may be affixed during the manufacturing process (e.g., by positioning it on stem 334 prior to sewing substantially inextensible textile element 340 to the distal end of stem 334).

Figure 14I:
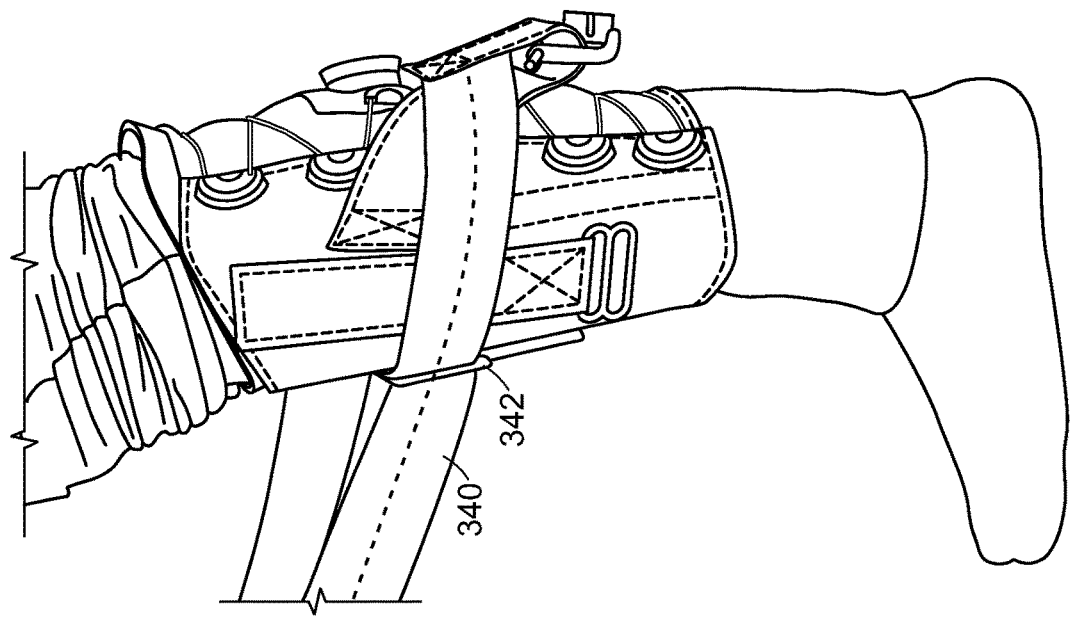
Figure 14H:
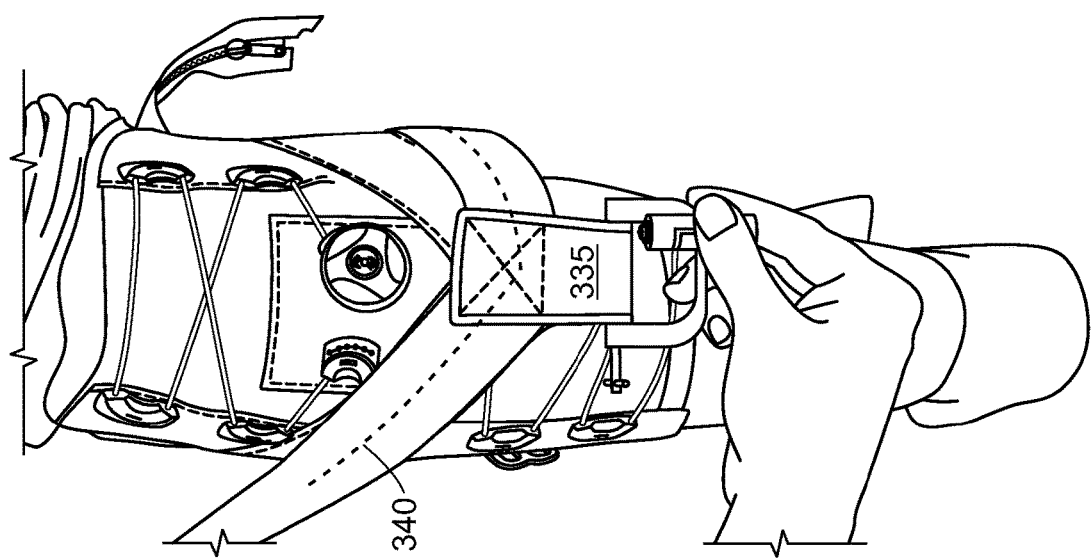

Referring to FIG. 14H, stem 334 is folded upwards to form the saddle 335. Substantially inextensible textile element 340 may then be aligned with the arms 332a, 332b of force transfer coupler 330 in preparation for being wrapped circumferentially around outer member body section 310.

Referring to FIG. 14I, substantially inextensible textile element 340 may be inserted through buckles 342 (if desired, as previously explained in the context of FIGS. 12A-12C), and wrapped around outer member body section 310.

Figure 14J:
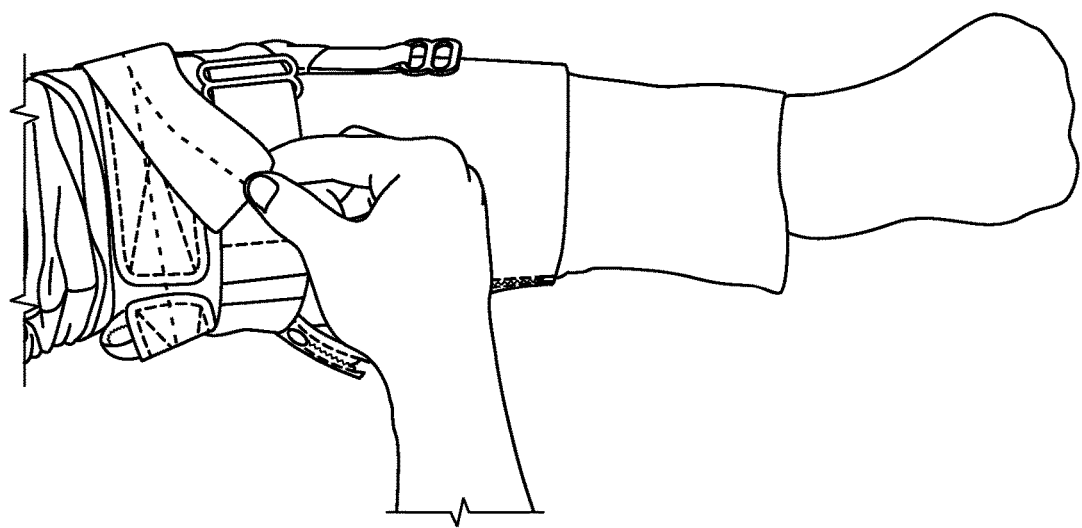

Referring to FIG. 14J, the distal ends substantially inextensible textile element 340 may be secured with Velcro or any other suitable fastener.

In another embodiment, a closed inner member is pulled or rolled on in a separate action from the donning of the outer member. Once in place, the outer member attaches via standardized attachment points on the inner member, and the process is followed as above.

All patents, patent applications, and published references cited herein are hereby incorporated by reference in their entirety. It will be appreciated that several of the above-disclosed and other features and functions, or alternatives thereof, may be desirably combined into many other different systems or applications. Various presently unforeseen or unanticipated alternatives, modifications, variations, or improvements therein may be subsequently made by those skilled in the art.

While the presently disclosed embodiments have been described with reference to certain embodiments thereof, it should be understood by those skilled in the art that various changes may be made and equivalents may be substituted without departing from the true spirit and scope of the presently disclosed embodiments. In addition, many modifications may be made to adapt to a particular situation, indication, material and composition of matter, process step or steps, without departing from the spirit and scope of the present presently disclosed embodiments. All such modifications are intended to be within the scope of the claims appended hereto.

What is claimed is:

1. A flexible anchor member comprising:
a member for placement about a body part of a wearer;
at least one substantially inextensible textile element partially or fully circumscribing a portion or all of the member and configured in one or more locations to be secured to itself or to the member; and
a force transfer coupler including two arms fixedly coupled to the member and a stem fixedly coupled to the at least one substantially inextensible textile element, wherein upon an actuator applying a force to the substantially inextensible textile element, the force transfer coupler is configured to cause the at least one substantially inextensible textile element to constrict about the member for a duration of the applied force.

2. The flexible anchor member according to claim 1, wherein the body part includes a waist, a thigh, a calf, a foot, a torso, an upper arm, a forearm, or a hand of the wearer.

3. The flexible anchor member according to claim 1, wherein the member is substantially planar and includes one or more fasteners for securing the member about the body part.

4. The flexible anchor member according to claim 1, wherein the member is substantially cylindrical or substantially conical and configured to be pulled onto or rolled onto the body part.

5. The flexible anchor member according to claim 1, wherein the member includes a mechanism for adjustably applying a pre-compression force about the body part.

6. The flexible anchor member according to claim 1, wherein the member further includes at least one stiffening element for enhancing a longitudinal stiffness of the member.

7. The flexible anchor member according to claim 6, wherein the force transfer coupler is configured to couple the actuator to a central portion of the member or to an end of the member situated closest to the actuator.

8. The flexible anchor member according to claim 1, wherein constriction of the at least one substantially inextensible textile element about the member generates a compression force that acts on the member to resist migration of the member for the duration of the applied force.

9. The flexible anchor member according to claim 1, further including one or more fasteners for securing the at least one substantially inextensible textile element to itself or to the member.

10. The flexible anchor member according to claim 9, wherein the one or more fasteners are further configured for adjusting a length of the at least one substantially inextensible textile element available for constricting about the member in response to the applied force.

11. The flexible anchor member according to claim 1, wherein the force transfer coupler is configured to transfer a first portion of the applied force to the member and a second portion of the applied force to the at least one substantially inextensible textile element.

12. The flexible anchor member according to claim 11, further including one or more fasteners for securing the at least one substantially inextensible textile element to the member,
wherein the one or more fasteners are configured for adjusting a path followed by the at least one substantially inextensible textile element about the member, thereby adjusting an amount of friction generated between the at least one substantially inextensible textile element and the member as the at least one substantially inextensible textile element constricts about the member.

13. The flexible anchor member according to claim 12, wherein the one or more fasteners are configured for adjusting a ratio of the first portion of the applied force transferred to the member and the second portion of the applied force transferred to the at least one substantially inextensible textile element.

14. The flexible anchor member according to claim 1, further including at least one of an electrode, a sensor, and wiring embedded within or otherwise integrated into the member.

15. The flexible anchor member according to claim 1, wherein the member comprises an outer member, and wherein the outer member includes a substantially inextensible textile material which is configured for directing the force applied by the actuator to act upon all or a portion of the body part.

16. The flexible anchor member according to claim 1, wherein the force transfer coupler is configured to couple a portion of the at least one substantially inextensible textile element to the actuator.

17. A flexible anchor member comprising:
an outer member for placement about a body part, the outer member including a substantially inextensible textile material configured for directing a force applied by an actuator to act upon all or a portion of the body part;
an inner member for positioning between the body part and the outer member, a first surface of the inner member being configured for frictionally engaging the body part or any intervening clothing;
at least one coupler for coupling the outer member and the inner member;
at least one substantially inextensible textile element partially or fully circumscribing a portion or all of the outer member and configured in one or more locations to be secured to itself or to the outer member; and
a force transfer coupler including two arms fixedly coupled to the member and a stem fixedly coupled to the at least one substantially inextensible textile element,
wherein the force transfer coupler is configured to couple a portion of the at least one substantially inextensible textile element to an actuator such that a force applied by the actuator causes the at least one substantially inextensible textile element to constrict about the outer member for a duration of the applied force.

18. The flexible anchor member according to claim 17, wherein the body part includes a waist, a thigh, a calf, a foot, a torso, an upper arm, a forearm, or a hand of the wearer.

19. The flexible anchor member according to claim 17, wherein all or most of the outer member is made from the substantially inextensible textile material, and
wherein the substantially inextensible textile material is configured for directing the applied force substantially circumferentially around the body part.

20. The flexible anchor member according to claim 17, wherein the substantially inextensible textile material extends between a first location and a second location of the outer member so as to direct the applied force from the first location to the second location.

21. The flexible anchor member according to claim 20, wherein the second location of the outer member is associated with at least one of a bony anatomical feature of the body part and a portion of the body part having resilient tissue or muscle.

22. The flexible anchor member according to claim 17, wherein the inner member acts to resist migration of the outer member relative to the body part in response to one or a combination of the applied force and natural motion of the body part.

23. The flexible anchor member according to claim 17, wherein the at least one coupler is configured for selectably coupling and decoupling the outer member and the inner member.

24. The flexible anchor member according to claim 23, wherein the at least one coupler is selected from the group consisting of: a hook and loop fastener, a snap, a button, and a zipper.

25. The flexible anchor member according to claim 17, wherein the at least one coupler fixedly couples the outer member and the inner member.

26. The flexible anchor member according to claim 25, wherein the at least one coupler is selected from the group consisting of: sewn seams, adhesive, rivets, and a heat bond.

27. The flexible anchor member according to claim 17, wherein at least one of the outer member and the inner member is substantially planar and includes one or more fasteners, wherein the at least one of the outer member and the inner member are configured to be formed into a substantially cylindrical or substantially conical shape.

28. The flexible anchor member according to claim 17, wherein at least one of the outer member and the inner member is configured to be pulled onto or rolled onto the body part.

29. The flexible anchor member according to claim 17, wherein the outer member includes a mechanism for adjustably applying a compression force about the body part.

30. The flexible anchor member according to claim 17, wherein the outer member further includes at least one stiffening element for enhancing a longitudinal stiffness of the outer member.

31. The flexible anchor member according to claim 30, wherein the outer member is configured to couple to the actuator at a central portion of the outer member or at an end of the outer member situated closest to the actuator.

32. The flexible anchor member according to claim 17, wherein the first surface of the inner member includes an anti-slip material for enhancing a coefficient of friction of the first surface of the inner member.

33. The flexible anchor member according to claim 32, wherein the anti-slip material includes at least one of a polyurethane-coated fabric, a polyurethane-polyester blend material, silicone, and adhesive.

34. The flexible anchor member according to claim 17, wherein the inner member includes a second surface and a thickness between the first surface and the second surface, and
wherein the thickness varies along at least a portion of the inner member such that a shape of the first surface complements a specific geometry of the body part.

35. The flexible anchor member according to claim 34, wherein the body part is a calf of a wearer,
wherein the inner member is thicker in an area configured for placement against a belly of the calf muscle and is thinner in an area configured for placement against the tibial tuberosity.

36. The flexible anchor member according to claim 17, wherein an elastic modulus of the inner member varies along at least a portion of the inner member, and
wherein the variations in elastic modulus are configured to distribute, uniformly onto the body part, a force applied to the inner member by the outer member.

37. The flexible anchor member according to claim 17, wherein an elastic modulus of the inner member varies along at least a portion of the inner member, and
wherein the variations in the elastic modulus are configured to direct, onto a specific portion of the body part, a force applied to the inner member by the outer member.

38. The flexible anchor member according to claim 23, further comprising a second inner member for positioning between the body part and the outer member, and
wherein a shape of the second inner member is substantially similar to the inner member such that the inner member and the second inner member may be selectively interchanged for use with the outer member.

39. The flexible anchor member according to claim 38, wherein the inner member is configured to complement a specific geometry of the body part at a first stage of a physical rehabilitation program or a training program, and
wherein the second inner member is configured to complement a specific geometry of the body part at a second stage of the physical rehabilitation program or the training program.

40. The flexible anchor member according to claim 38, wherein the inner member is configured to complement a specific geometry of the body part of a first person, and
wherein the second inner member is configured to complement a specific geometry of the body part of a second person.

41. The flexible anchor member according to claim 17, further including at least one of an electrode, a sensor, and wiring embedded within or otherwise integrated into at least one of the outer member and the inner member.

42. The flexible anchor member according to claim 41, wherein the at least one of the electrode, the sensor, and the wiring is embedded within or otherwise integrated into both the inner member and the outer member, and
wherein the at least one coupler provides an electrical connection between the at least one of the electrode, the sensor, and the wiring embedded within or otherwise integrated into the inner member and the outer member.

* * * * *

UNITED STATES PATENT AND TRADEMARK OFFICE
CERTIFICATE OF CORRECTION

PATENT NO. : 11,590,046 B2
APPLICATION NO. : 16/084377
DATED : February 28, 2023
INVENTOR(S) : Kathleen E. O'Donnell et al.

Page 1 of 1

It is certified that error appears in the above-identified patent and that said Letters Patent is hereby corrected as shown below:

In the Specification

At Column 1, Lines 18-22, STATEMENT REGARDING FEDERALLY SPONSORED RESEARCH OR DEVELOPMENT section please change the sentences:
"At least some of the aspects of the presently disclosed embodiments were made with government support from the Defense Advanced Research Projects Agency (DARPA), under Grant W911NF-14-C0051. The government shares rights to such aspects of the invention."

To:
--This invention was made with government support under Grant No. W911NF-14-C0051 awarded by the Defense Advanced Research Projects Agency (DARPA). The government has certain rights in this invention.--

Signed and Sealed this
Eighteenth Day of April, 2023

Katherine Kelly Vidal
*Director of the United States Patent and Trademark Office*